United States Patent
Togashi et al.

(10) Patent No.: US 7,500,386 B2
(45) Date of Patent: Mar. 10, 2009

(54) SAMPLE INJECTION APPARATUS AND LIQUID CHROMATOGRAPHY APPARATUS HAVING THE SAMPLE INJECTION APPARATUS

(75) Inventors: Yuki Togashi, Yokohama (JP); Osamu Shirota, Yokohama (JP); Aya Ohkubo, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 12/068,202

(22) Filed: Feb. 4, 2008

(65) Prior Publication Data
US 2008/0141762 A1  Jun. 19, 2008

Related U.S. Application Data

(63) Continuation of application No. 10/556,391, filed as application No. PCT/JP2004/006555 on May 14, 2004, now Pat. No. 7,337,653.

(30) Foreign Application Priority Data

May 15, 2003 (JP) .............................. 2003-137881
Mar. 3, 2004 (JP) .............................. 2004-059713

(51) Int. Cl.
*G01N 30/16* (2006.01)

(52) U.S. Cl. .................... 73/61.55; 73/61.52; 73/61.56; 73/864.21; 73/864.25; 73/864.87

(58) Field of Classification Search .............. 73/61.52, 73/61.55, 61.56, 61.59, 864.21, 864.25, 864.84, 73/864.87
See application file for complete search history.

(56) References Cited

U.S. PATENT DOCUMENTS

| 2,852,417 | A | 9/1958 | Kearney |
| 2,992,142 | A | 7/1961 | Kearney |
| 4,216,671 | A | 8/1980 | Kurland |
| 5,056,464 | A | 10/1991 | Lewis |
| 6,328,828 | B1 | 12/2001 | Rusczyk |
| 6,474,350 | B1 | 11/2002 | Mizuta |

(Continued)

FOREIGN PATENT DOCUMENTS

CN    2133370 Y    5/1993

(Continued)

OTHER PUBLICATIONS

"B3 Ultrasonic Cleaner", http://www.bransonic.com/model_b3.asp.

(Continued)

*Primary Examiner*—Daniel S Larkin
(74) *Attorney, Agent, or Firm*—IPUSA, PLLC

(57) ABSTRACT

A sample injection apparatus and a liquid chromatography apparatus including the sample injection apparatus are provided. The sample injection apparatus includes a sampling vessel into which a sample is supplied, a sampling needle for aspirating and ejecting the sample, a cleaning part into which a cleaning liquid for cleaning at least the sampling needle is supplied, a sample injection part for injecting the sample ejected from the sampling needle into a moving liquid, and a needle transfer part for transferring the sampling needle among the sampling vessel, the cleaning part and the sample injection part, wherein the cleaning part includes an ultrasonic vibrator for generating an ultrasonic wave in the cleaning liquid.

8 Claims, 14 Drawing Sheets

U.S. PATENT DOCUMENTS

| | | |
|---|---|---|
| 6,759,014 B2 | 7/2004 | Dales et al. |
| 2002/0102185 A1 | 8/2002 | Tatsumi |
| 2003/0131869 A1 | 7/2003 | Glucksman et al. |

FOREIGN PATENT DOCUMENTS

| | | |
|---|---|---|
| EP | 1 226 867 A | 7/2002 |
| JP | 01-254871 | 10/1989 |
| JP | 08-254538 | 10/1996 |
| JP | 09-021730 | 1/1997 |
| JP | 11-304779 | 11/1999 |
| JP | 2001-170538 A | 6/2001 |
| JP | 2004-325398 A | 11/2004 |
| WO | WO 01/94003 A | 12/2001 |

OTHER PUBLICATIONS

Supplementary European Search Report.
Anonymous: "P-08849-00—One-Pint Compact Cleaner" [Online] XP002468563 Cole-Parmer Retrieved from the Internet :URL: http://www.coleparmer.com/catalog/product_view . . . .

FIG.10
(a)
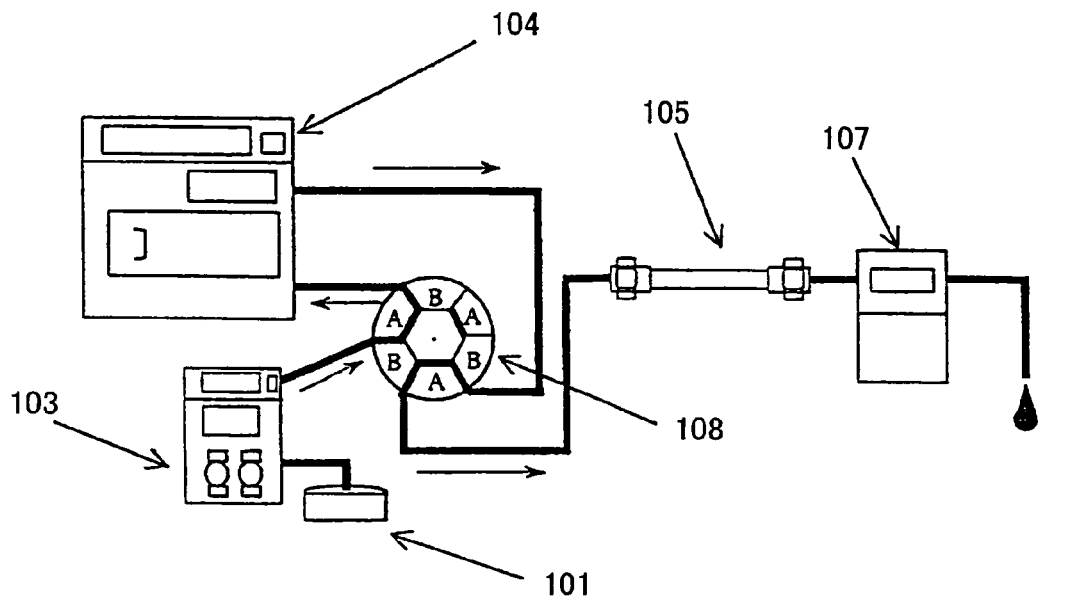
(b)
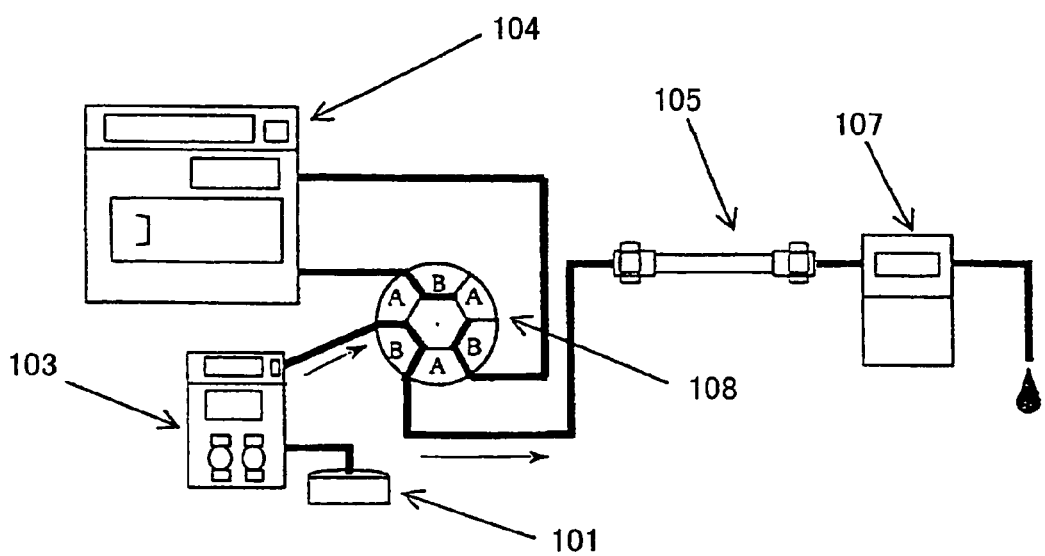

FIG.13
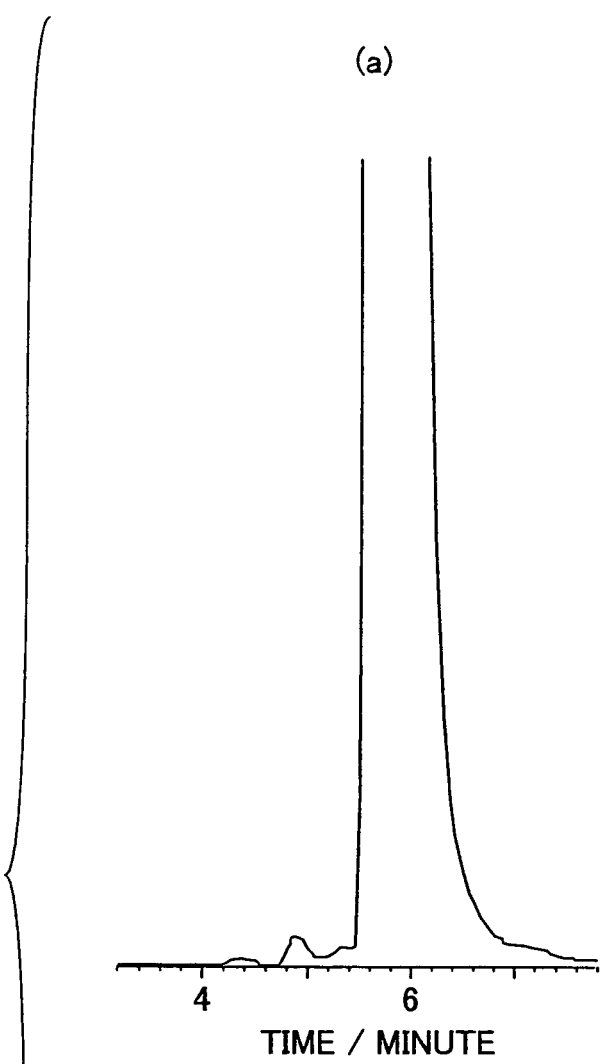
(a)
TIME / MINUTE
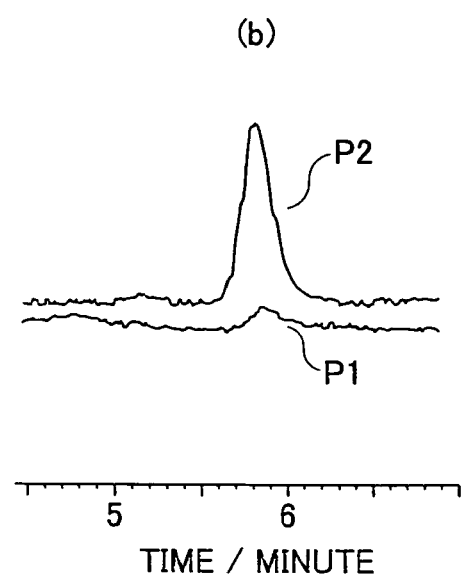
(b)
P2
P1
TIME / MINUTE

SAMPLE INJECTION APPARATUS AND LIQUID CHROMATOGRAPHY APPARATUS HAVING THE SAMPLE INJECTION APPARATUS

RELATED APPLICATIONS

This application is a continuation of U.S. patent application Ser. No. 10/556,391, filed on Nov. 10, 2005 now U.S. Pat. No. 7,337,653, which was the national stage application of PCT/JP2004/006555, filed on May 14, 2004, claiming the priority of JP 2003-137881 (filed on May 14, 2003) and JP 2004-059713 (filed on March 3, 2004). The instant application claims the priority of these applications and incorporates them by reference.

TECHNICAL FIELD

The present invention relates to a sample injection apparatus and sample injection method for injecting a sample into moving liquid and a liquid chromatography apparatus having the sample injection apparatus.

BACKGROUND ART

A liquid chromatography apparatus for pressurizing a sample with liquid as a mobile phase so as to send them to a column, separating and eluting components of the sample and detecting them on a detector basically has a configuration as shown in FIG. 4. In FIG. 4, the liquid chromatography apparatus includes a mobile phase reservoir 101 for storing the liquid as a mobile phase, a mobile phase degassing device 102 for removing air from the liquid as a mobile phase, a pump 103 for sending the liquid as a mobile phase from the mobile phase reservoir 101 to a detector 107, an (automatic) sample injection apparatus 104 for injecting a sample into the liquid as a mobile phase directed into a separation column 105, the separation column 105 being filled with a packing material for separating components of the sample, a column thermostatic bath 106 for keeping the temperature of the separation column 105 to be approximately constant, and the detector 107 for detecting an eluted component of the sample.

As the detection sensitivity of a liquid chromatography apparatus having such a structure becomes higher, a phenomenon called carry-over has become problematic. The carry-over is a phenomenon such that a substance of a sample measured previously through time remains in the liquid chromatography apparatus so as to show a detection result as if the substance were present in the sample measured at present, and reduces the reliability of the results of analysis. The carry-over is caused, when a sample is adsorbed on a metal and/or a resin and remains in the automatic sample injection apparatus 104 after the sample is injected into the liquid as a mobile phase in the automatic sample injection apparatus 104, and the remaining sample is introduced into the liquid chromatography analysis system when a next sample is introduced. Particularly, it is known that a sample containing a basic and/or fat-soluble substance is easily adsorbed on the metal and/or resin in the automatic sample injection apparatus 104 and, therefore, easily remains in the automatic sample injection apparatus 104 so that carry-over is significantly observed.

In order to reduce the carry-over by removing the sample adsorbed and remaining in the automatic sample injection apparatus 104, a self-cleaning function can be provided in the automatic sample injection apparatus 104. As shown in FIG. 6, the main operation of the automatic sample injection apparatus 104 is composed of sampling a sample supplied into a sampling vessel 14 by a sampling needle 10, inserting the sampling needle 10 in which the sample is sampled into an injection port 19 of an injection valve 15 so as to inject the sample from the sampling needle 10 through a sample injection route to a sample loop 16, and switching flow channels for a sample in the injection valve 15 so as to send the sample in the sample loop 16 to the separation column 105. Therefore, as locations (sample adsorbing portions) at which the sample in the automatic sample injection apparatus 104 is adsorbed and remains, an outer wall of the sampling needle 10 after sampling the sample, an inner wall of the sampling needle 10 after sampling the sample, an inner wall of the sample loop 16 after sending the sample to the separation column 105, and the flow channel for a sample in the injection valve 15 are listed.

Since the self-cleaning functions are provided to these sample adsorbing portions, it is only necessary to provide four self-cleaning functions, that is, a function for cleaning the outer wall of the sampling needle, a function for cleaning the inner wall of the sampling needle, and functions for cleaning the sample loop and the injection valve. These four self-cleaning functions are described below.

(1) The function for cleaning the outer wall of the sampling needle immediately before sample injection (Needle pre-washing)

As shown in FIG. 7, needle pre-washing is a function for removing a sample adsorbed and remaining on the outer wall of the sampling needle 10 after sampling the sample by dipping the sampling needle 10 into cleaning liquid that is sent into a cleaning part 17 immediately before the sample sampled in the sampling needle 10 is injected into an injection port. The cleaning liquid used for removing the sample remaining on the outer wall of the sampling needle 10 is disposed of and pure cleaning liquid is supplied into the cleaning part 17. For the needle pre-washing, a user can set a time period (cleaning time period) for dipping the sampling needle 10 in the cleaning liquid.

(2) The function for cleaning the inner wall of the sampling needle immediately after sample injection (Needle post-washing)

As shown in FIG. 8, needle post-washing is a function for removing a sample adsorbed and remaining on the inner wall of the sampling needle 10 by dipping the sampling needle 10 into cleaning liquid supplied into the cleaning part 17 and flowing the cleaning liquid through the sampling needle 10 immediately after the sample is injected into the injection port. The cleaning liquid used for removing the sample remaining on the inner wall of the sampling needle 10 is disposed of and pure cleaning liquid is supplied into the cleaning part 17. For the needle post-washing, a user can set a time period (cleaning time period) for flowing the cleaning liquid through the sampling needle 10.

(3) The cleaning of the sample injection route after the sample injection (Post-injection washing)

As show in FIG. 9, the post-injection washing is a cleaning function in which after a sample is injected into an injection port, operations (1) through (3) are carried out in order during the analysis of the sample.

1) The sampling needle 10 is moved to a position above a cleaning port 24 and cleaning liquid prepared in the cleaning port 24 is aspirated into the sampling needle 10.

2) The sampling needle 10 that aspirated and holds the cleaning liquid is inserted into the injection port 19 of the injection valve 15 and the cleaning liquid in the sampling needle 10 is (repeatedly) ejected and aspirated so as to clean a sample injection route (flow channel from the injection port 19 to a waste liquid disposal port 23) in the injection valve 15. At this time, the injection port 19 and the waste liquid disposal port 23 are connected and the injection port 19 is not connected to the sample loop 16 in the injection valve 15. Therefore, as the injection port 19 and the waste liquid disposal port 23 are connected after injecting a sample into the sample injection route, while the sample is analyzed through the sample loop 16, a flow channel between the injection port 19 and the waste liquid disposal port 23 can be cleaned.

3) For the post-injection washing, a user can set the volume of cleaning liquid to be aspirated into the sampling needle 10 and the number of ejections and aspirations of the cleaning liquid (the number of cleanings). Also, two or more cleaning liquid ports 24 can be provided so as to use two or more kinds of cleaning liquids. For example, when the two or more kinds of cleaning liquids are used, if a previously used cleaning liquid is liquid with high detergency (a strong alkali that is not desired to pass through the separation column 15, etc.) and a subsequently used cleaning liquid is liquid to be used as a mobile phase, the liquid with high detergency can be used and the liquid with high detergency can be prevented from mixing into an analysis system.

(4) A function of cleaning the sample loop and the injection valve during the progression of analysis (Loop rinse)

For performing the loop rinse, a loop rinse valve is required except for the automatic sample injection apparatus. As shown in FIGS. 10(a) and 10(b), a loop rinse valve 108 operates so as to switch flow channels of liquid as a mobile phase supplied from the mobile phase reservoir 101. That is, as shown in FIG. 10(a), when the cleaning function of the loop rinse is not performed, the liquid as the mobile phase sent out by the pump 103 is supplied into the sample injection apparatus 104 and sent to the separation column 105 and the detector 107 with a sample. On the other hand, as shown in FIG. 10(b), when the cleaning function of the loop rinse is performed, the liquid as the mobile phase sent out by the pump 103 does not pass through the sample injection apparatus 104 and is directly sent to the separation column 105 and the detector 107. As such a loop rinse valve 108 is used, if after sending the sample to the separation column 105 through a flow channel shown in FIG. 10(a), immediately switching to a flow channel shown in FIG. 10(b) is made, while analysis is progressed by sending the liquid as the mobile phase to the separation column 105, the sample loop and the injection valve can be cleaned.

The loop rinse is a cleaning function for carrying out the following operations 1) through 4) in order after injecting a sample into the sample loop 16, as shown in FIG. 10 and FIG. 11.

1) After the sample is injected into the sample loop 16, the automatic sample injection apparatus is completely separated from a flow channel of an analysis system including the separation column 105 and the detector 107 by the loop rinse valve 108.

2) While analysis is carried out by sending the liquid as the mobile phase to the separation column without traveling through the automatic sample injection apparatus 104, the insides of the sample loop 16 and injection valve 15 are cleaned by inserting the sampling needle 10 into the injection port 19 of the injection valve 15 and ejecting the cleaning liquid from the sampling needle 10 in the automatic sample injection apparatus 104. Then, the sampling needle 10 is connected to a cleaning liquid reservoir in which the cleaning liquid is stored and the cleaning liquid is supplied to the sampling needle from the cleaning liquid reservoir.

3) Since the flow channels of the injection valve 15 are switched while the cleaning liquid is ejected from the sampling needle, a flow channel from the injection port 19 to the waste liquid disposal port 23 can be also cleaned.

4) As the cleaning in the sample loop 16 and the injection valve 15 is completed, the loop rinse valve 108 is switched to the usual flow channel through the automatic sample injection apparatus 104, again, as shown in FIG. 10(a).

For the loop rinse, a user can set a time period of ejecting the cleaning liquid from the sampling needle 10 (cleaning time period) and the number of times of switching of the injection valve 15. Also, two or more vessels for cleaning liquid can be provided so that two or more kinds of cleaning liquids can be used by connecting these vessels for cleaning liquid to the sampling needle 10 and switching the connections among these vessels for cleaning liquids and the sampling needle 10. For example, when the two or more kinds of cleaning liquids are used, if previously used cleaning liquid is liquid with high detergency (a strong alkali that is not desired to pass through the separation column 105, etc.) and subsequently used cleaning liquid is liquid to be used as a mobile phase, the liquid with high detergency can be used and the liquid with high detergency can be prevented from mixing into an analysis system.

On the other hand, in regard to cleaning of a needle, a sample introduction apparatus for introducing a sample to an analyzer such as a liquid chromatography apparatus, which sample introduction apparatus can perform the mixing of samples or the cleaning of needle without aspirating or ejecting liquid, is also disclosed in JP-A-11-304779. This sample introduction apparatus is equipped with a vibration generation part such as an ultrasonic vibrator arranged directly or through the intermediary of a member capable of transmitting the vibration, on a sample injection needle, and a vibration control part for controlling the vibration generation part. More specifically, it is equipped with an ultrasonic vibrator arranged in connection with the sample injection needle or a metal part connecting to the sample injection needle, and the needle itself is vibrated by the ultrasonic vibrator which is simultaneously controlled by the vibration control part, at the time of mixing the samples or cleaning the needle.

Since the automatic sample injection apparatus provided with four self-cleaning functions performs the four self-cleaning functions in combination in order to reduce a carry-over phenomenon, a cleaning time period of approximately 3 minutes on average is needed. Among these four self-cleaning functions, the needle pre-washing is performed before the start of analysis but cleaning for approximately 1 through 5 seconds is commonly sufficient so that a shorter cleaning time period is required. Therefore, the three self-cleaning functions other than the needle pre-washing require approximately 3 minutes in total. However, these three self-cleaning functions are practicable while a sample is analyzed. Accordingly, if the time period of analysis is 3 minutes or more, all the three self-cleaning functions are carried out within the time period of analysis, in which there is no problem. However, in regard to analysis by means of liquid chromatography, the time period of analysis is being reduced and the cleaning time period has to be reduced (for example, to a cleaning time period=1 minute or less) in accordance with the reduction of the time period of analysis.

Also, it is necessary to set the operating conditions of the four self-cleaning functions, respectively, in the automatic sample injection apparatus provided with the four self-cleaning functions, in order to set the optimum cleaning conditions adapted to a sample to be analyzed. However, as described above, since it is necessary to set approximately 6 through 8 parameters in total for the operating conditions of the four self-cleaning functions, the number of the parameters to be set is high, which is complex and inconvenient for a user.

On the other hand, in regard to the sample introduction apparatus provided with a vibration generation part such as an ultrasonic vibrator arranged directly or through the intermediary of a member capable of transmitting the vibration, on a sample injection needle, since the sample injection needle itself is vibrated, adverse impact is applied to the sample injection needle. As the result, it is a concern that the deterioration of the sample injection needle is caused and the durability of the sample injection needle is lowered. Also, as the sample injection needle is cleaned on the condition that a sample is held in such a sample injection needle, since the sample injection needle itself vibrates, a part of the sample held in the sample injection needle is lost in the cleaning liquid and there is a possibility of causing a large error in the amount of injected sample. Further, there is also a possibility of transmitting vibration through the sample injection needle to another member of the automatic sample injection apparatus by vibrating the sample injection needle itself. However, since the automatic sample injection apparatus is fundamentally a precision machine, it is required to avoid undesired vibration. Therefore, there is also a problem in that the sample introduction apparatus provided with a vibration generation part such as an ultrasonic vibrator arranged directly or through the intermediary of a member capable of transmitting the vibration on a sample injection needle, can be influenced by the ultrasonic vibration of the sample injection needle.

DISCLOSURE OF THE INVENTION

The objects of the present invention are to provide a sample injection apparatus and sample injection method capable of sufficiently reducing carry-over, having simple cleaning means for a short cleaning time period, a small influence of vibration of the cleaning means, and a small error in the amount of injected sample and preventing the durability of a sampling needle from being lowered, and a liquid chromatography apparatus having the sample injection apparatus.

One of the objects is achieved by a sample injection apparatus having a sampling vessel into which a sample is supplied, a sampling needle for aspirating and ejecting the sample, a cleaning part into which a cleaning liquid for cleaning at least the sampling needle is supplied, a sample injection part for injecting the sample ejected from the sampling needle into a moving liquid, and needle transfer means for transferring the sampling needle among the sampling vessel, the cleaning part and the sample injection part, wherein the cleaning part has an ultrasonic vibrator for generating an ultrasonic wave in the cleaning liquid.

According to the sample injection apparatus, a sample injection apparatus capable of sufficiently reducing carry-over, having simple cleaning means for a short cleaning time period, a small influence of vibration of the cleaning means, and a small error in the amount of injected sample and preventing the durability of a sampling needle from being lowered can be provided, since the cleaning part has an ultrasonic vibrator for generating an ultrasonic wave in the cleaning liquid.

In the sample injection apparatus, preferably, the cleaning part has a vibration buffer member for reducing propagation of vibration caused by the ultrasonic vibrator to a member other than the cleaning part in the sample injection apparatus.

According to the sample injection apparatus, the influence of vibration caused by the ultrasonic vibrator to a member other than the cleaning part in the sample injection apparatus can be further reduced, since the cleaning part has a vibration buffer member for reducing propagation of vibration caused by the ultrasonic vibrator to a member other than the cleaning part in the sample injection apparatus.

In the sample injection apparatus, preferably, a vibration frequency of the ultrasonic vibrator is 20 kHz or more and 80 kHz or less.

According to the sample injection apparatus, a sample injection apparatus that can reduce carry-over more efficiently can be provided, since a vibration frequency of the ultrasonic vibrator is 20 kHz or more and 80 kHz or less.

In the sample injection apparatus, preferably, an inner diameter of the sampling needle is 0.1 mm or more and 0.8 mm or less.

According to the sample injection apparatus, a sample injection apparatus that can reduce loss of a sample can be provided, since an inner diameter of the sampling needle is 0.1 mm or more and 0.8 mm or less.

One of the objects is achieved by a sample injection method having a step of aspirating a sample into a sampling needle, a step of holding the sample in the sampling needle and dipping the sampling needle in cleaning liquid, a step of generating an ultrasonic wave in the cleaning liquid so as to clean the sampling needle dipped in the cleaning liquid, and a step of ejecting the sample from the sampling needle so as to inject the sample into a moving liquid.

According to the sample injection method, a sample injection method capable of sufficiently reducing carry-over, having simple cleaning means for a short cleaning time period, a small influence of vibration of the cleaning means, and a small error in the amount of injected sample and preventing the durability of a sampling needle from being lowered can be provided, because of having a step of aspirating a sample into a sampling needle, a step of holding the sample in the sampling needle and dipping the sampling needle in cleaning liquid, a step of generating an ultrasonic wave in the cleaning liquid so as to clean the sampling needle dipped in the cleaning liquid, and a step of ejecting the sample from the sampling needle so as to inject the sample into a moving liquid.

In the sample injection method, preferably, a vibration frequency of the ultrasonic vibrator is 20 kHz or more and 80 kHz or less.

According to the sample injection method, a sample injection method that can reduce carry-over more efficiently can be provided, since a vibration frequency of the ultrasonic vibrator is 20 kHz or more and 80 kHz or less.

In the sample injection method, preferably, an inner diameter of the sampling needle is 0.1 mm or more and 0.8 mm or less.

According to the sample injection method, a sample injection method that can reduce loss of a sample can be provided, since an inner diameter of the sampling needle is 0.1 mm or more and 0.8 mm or less.

One of the objects is achieved by a liquid chromatography apparatus having a mobile phase reservoir for storing a liquid as a mobile phase, a sample injection apparatus for injecting a sample into the liquid as a mobile phase, a separation column for separating a component of the sample sent from the sample injection apparatus and the liquid as a mobile phase, and a detector for detecting a component of the sample separated by the separation column, in which the sample injection apparatus has a sampling vessel into which a sample is supplied, a sampling needle for aspirating and ejecting the sample, a cleaning part into which cleaning liquid for cleaning at least the sampling needle is supplied, a sample injection part for injecting the sample ejected from the sampling needle into the liquid as a mobile phase, and needle transfer means for transferring the sampling needle among the sampling vessel, the cleaning part and the sample injection part, wherein the cleaning part has an ultrasonic vibrator for generating an ultrasonic wave in the cleaning liquid.

According to the liquid chromatography apparatus, a liquid chromatography apparatus can be provided which has a sample injection apparatus capable of sufficiently reducing carry-over, having simple cleaning means for a short cleaning time period, a small influence of vibration of the cleaning means, and a small error in the amount of injected sample and preventing the durability of a sampling needle from being lowered can be provided, since the sample injection apparatus has a sampling vessel into which a sample is supplied, a sampling needle for aspirating and ejecting the sample, a cleaning part into which cleaning liquid for cleaning at least the sampling needle is supplied, a sample injection part for injecting the sample ejected from the sampling needle into the liquid as a mobile phase, and needle transfer means for transferring the sampling needle among the sampling vessel, the cleaning part and the sample injection part, wherein the cleaning part has an ultrasonic vibrator for generating an ultrasonic wave in the cleaning liquid.

In the liquid chromatography apparatus, preferably, the cleaning part has a vibration buffer member for reducing propagation of vibration caused by the ultrasonic vibrator to a member other than the cleaning part in the sample injection apparatus.

According to the liquid chromatography apparatus, the influence of vibration caused by the ultrasonic vibrator to a member other than the cleaning part in the sample injection apparatus can be further reduced, since the cleaning part has a vibration buffer member for reducing propagation of vibration caused by the ultrasonic vibrator to a member other than the cleaning part in the sample injection apparatus.

In the liquid chromatography apparatus, preferably, a vibration frequency of the ultrasonic vibrator is 20 kHz or more and 80 kHz or less.

According to the liquid chromatography apparatus, a liquid chromatography apparatus having a sample injection apparatus that can reduce carry-over more efficiently can be provided, since a vibration frequency of the ultrasonic vibrator is 20 kHz or more and 80 kHz or less.

In the liquid chromatography apparatus, preferably, an inner diameter of the sampling needle is 0.1 mm or more and 0.8 mm or less.

According to the liquid chromatography apparatus, a liquid chromatography apparatus that can reduce loss of a sample can be provided, since an inner diameter of the sampling needle is 0.1 mm or more and 0.8 mm or less.

BRIEF DESCRIPTION OF THE DRAWINGS

FIG. 10 is a diagram illustrating the operation of a loop rinse valve in the loop rinse, (a) is a diagram showing the case of not-operating the cleaning function of the loop rinse and (b) is a diagram showing the case of operating the cleaning function of the loop rinse.

FIG. 13 is a diagram showing an evaluation result for carry-over which was performed for a liquid chromatography apparatus including an automatic sample injection apparatus in accordance with a direct injection approach, wherein (a) is a peak for a sample and (b) is a diagram showing detection results in the case of performing ultrasonic cleaning and the case of not-performing ultrasonic cleaning.

BEST MODE FOR CARRYING OUT THE INVENTION

Figure 1:
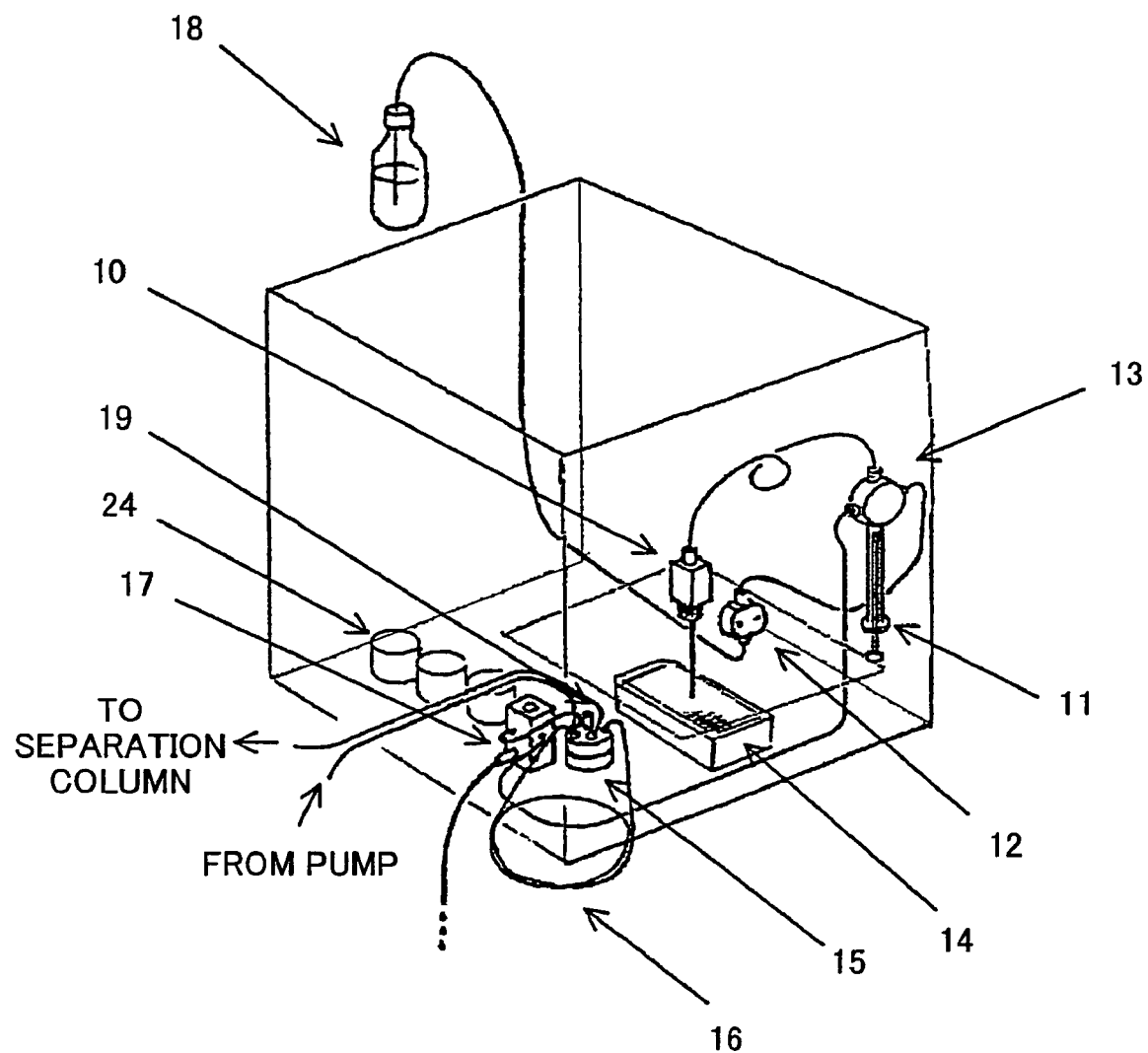
FIG. 1 is a diagram showing an automatic sample injection apparatus according to the present invention.

An embodiment of the present invention is illustrated with reference to the drawings below.

First, the structure of a sample injection apparatus according to the present invention is described. The sample injection apparatus according to the present invention includes at least a sampling vessel, a sampling needle, a cleaning part, a sample injection part, and needle transfer means.

A sample to be injected into moving liquid is supplied into and stored in the sampling vessel. The sampling needle aspirates and ejects the sample to be injected into moving liquid. For example, the sampling needle is connected to a syringe and the sample is aspirated and ejected by controlling the internal pressure of the sampling needle due to push and pull of the syringe. Cleaning liquid for cleaning at least the sampling needle is supplied into the cleaning part. The cleaning liquid that is supplied into the cleaning part may be used for cleaning not only the sampling needle but also, for example, a sample injection route in an injection valve and a sample loop as described above. Also, the cleaning liquid may be the same liquid as the moving liquid. In the cleaning part, pure cleaning liquid is continuously supplied and the cleaning liquid contaminated by cleaning the sampling needle, etc., is wasted. The sample injection part is a member for injecting the sample ejected from the sampling needle into liquid moving in the sample injection apparatus according to the present invention. More specifically, the sample injection part includes an injection valve and a sample loop as described above, etc. The needle transfer means transfers the sampling needle among the sampling vessel, the cleaning part and the sample injection part. The needle transfer means may singularly transfer the sampling needle to the sampling vessel, the cleaning part and the sample injection part. Alternatively, the needle transfer means may be different means for the transfer of the sampling needle between the sampling vessel and the cleaning part and for the transfer of the sampling needle between the cleaning part and the sample injection part.

According to the present invention, the cleaning part has an ultrasonic vibrator for generating an ultrasonic wave in the cleaning liquid and is made of a material that can transmit the ultrasonic wave generated by vibration of the ultrasonic vibrator. The ultrasonic vibrator can be attached at any place in the cleaning part (for example, the bottom face of the cleaning part) on which place the ultrasonic vibrator can vibrate freely. The vibration of the ultrasonic vibrator can be controlled by a device for controlling the vibration of the ultrasonic vibrator. The vibration of the ultrasonic vibrator generates an ultrasonic wave in the cleaning liquid stored in the cleaning part. The ultrasonic wave generated by the ultrasonic vibrator is an incoherent compressional wave and is reflected from an inner wall of the cleaning part, so as to vibrate the cleaning liquid in the neighborhood of an outer wall of the sampling needle dipped in the cleaning liquid. Accordingly, the sample adsorbed or remaining on the outer wall of the sampling needle can be removed.

In the sample injection apparatus according to the present invention, since the ultrasonic vibrator is not attached (directly or through the intermediary of a member capable of transmitting the vibration) to the sampling needle itself, the sampling needle itself is not vibrated. Therefore, there is no adverse impact caused by the vibration of the ultrasonic vibrator on the sampling needle in the present invention and cleaning of the sampling needle by means of an ultrasonic wave can be realized without deteriorating the sampling needle (without lowering the durability of the sampling needle). Also, since the sampling needle itself does not vibrate, even if the sampling needle is subjected to the ultrasonic cleaning after aspirating a sample, loss of the aspirated sample in the cleaning liquid is low and an error in the amount of the sample to be injected into the moving liquid is low. Therefore, the sample can be precisely injected into the moving liquid. Further, since the sampling needle itself is not vibrated, there is no propagation of the vibration to other members of the sample injection apparatus through the intermediary of the sampling needle, so that vibration of the sample injection apparatus caused by the vibration of the sampling needle can be prevented.

It is desirable that the cleaning part have a vibration buffer member. This vibration buffer member reduces the propagation of the vibration caused by the ultrasonic vibrator to a member other than the cleaning part in the sample injection apparatus. Accordingly, adverse effect caused by the vibration of the ultrasonic vibrator on the member other than the cleaning part in the sample injection apparatus can be reduced. For example, the vibration buffer member is an elastic body such as a spring and rubber. Also, when vibration caused by the ultrasonic vibrator is not propagated to the member other than the cleaning part in the sample injection apparatus, the energy of vibration caused by the ultrasonic vibrator is not wasted and can be effectively used for cleaning the sampling needle.

It is preferable that a vibration frequency of the ultrasonic vibrator be 20 kHz or more and 80 kHz or less. If the vibration frequency of the ultrasonic vibrator is less than 20 kHz, it is necessary to increase the volume of the cleaning liquid stored in the cleaning part in order to sufficiently generate an ultrasonic stationary wave in the cleaning liquid stored in the cleaning part. Therefore, the size of the sample injection apparatus including the cleaning part and the size of the liquid chromatography apparatus including the sample injection apparatus have to be increased. On the other hand, if the vibration frequency of the ultrasonic vibrator is more than 80 kHz, a larger size and special ultrasonic vibrator is needed in order to sufficiently generate an ultrasonic stationary wave in the cleaning liquid stored in the cleaning part. Consequently, as the vibration frequency of the ultrasonic vibrator is 20 kHz or more and 80 kHz or less, an ultrasonic stationary wave can be generated more easily in the cleaning liquid stored in the cleaning part. Also, if the vibration frequency of the ultrasonic vibrator is less than 20 kHz or more than 80 kHz, the efficiency of reducing carry-over is slightly lowered. On the contrary, when the vibration frequency of the ultrasonic vibrator is 20 kHz or more and 80 kHz or less, the carry-over can be reduced more efficiently.

Also, it is important that the size of the cleaning part in the direction of the transmission of ultrasonic vibration in the cleaning liquid is not too small relative to the wavelength of ultrasonic stationary wave generating in the cleaning liquid, and preferably, the size of the cleaning part in the direction of the transmission of ultrasonic vibration is larger than the wavelength of ultrasonic stationary wave generating in the cleaning liquid. In this case, the ultrasonic stationary wave can generate stably in the cleaning liquid stored in the cleaning part and the sample adsorbed and remaining on the outer wall of the sampling needle can be removed efficiently.

Further, it is preferable that an inner diameter of the sampling needle be significantly smaller than the wavelength of the ultrasonic stationary wave generating in the cleaning liquid stored in the cleaning part. When the inner diameter of the sampling needle is significantly smaller than the wavelength of the ultrasonic stationary wave generating in the cleaning liquid stored in the cleaning part, an ultrasonic stationary wave does not generate in a liquid sample held in the sampling needle and there is no loss of the liquid sample held in the sampling needle which loss is caused by the ultrasonic wave. As the result, the sample adsorbed and remaining on the outer wall of the sampling needle can be removed without the loss of the liquid sample held in the sampling needle which loss is caused by the ultrasonic wave. On the contrary, as the inner diameter of the sampling needle approximates the wavelength of the ultrasonic stationery wave being generated in the cleaning liquid stored in the cleaning part, the ultrasonic wave may generate in the liquid sample held in the sampling needle so as to cause the loss of a part of the liquid sample held in the sampling needle.

Figure 14:
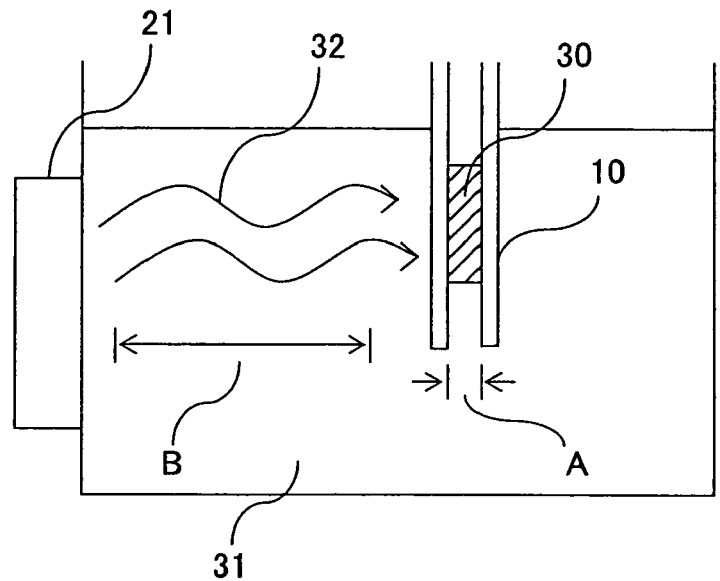
FIG. 14 is a diagram illustrating the relation between the inner diameter of a sampling needle and ultrasonic stationary wave generating in cleaning liquid.

FIG. 14 is a diagram illustrating the relation between the inner diameter of the sampling needle and the ultrasonic stationary wave generating in the cleaning liquid. As shown in FIG. 14, for example, when the vibration frequency of an ultrasonic vibrator 21 is 20 kHz or more and 80 kHz or less, it is preferable that the inner diameter A of the sampling needle 10 be 0.1 mm or more and 0.8 mm or less. When the inner diameter A of the sampling needle 10 is 0.8 mm or less, the inner diameter A of the sampling needle 10 is less than the wavelength B of ultrasonic stationary wave 32 generated in cleaning liquid 31 stored in the cleaning part. Therefore, the sample adsorbed and remaining on the outer wall of the sampling needle 10 can be removed without the loss of liquid sample 30 held in the sampling needle, which loss is caused by an ultrasonic wave. On the other hand, when the vibration frequency of the ultrasonic vibrator 21 is 20 kHz or more and 80 kHz or less and the inner diameter A of the sampling needle 10 is more than 0.8, a part of the liquid sample 30 held in the sampling needle 10 may be lost. Also, the inner diameter A of the sampling needle 10 is 0.1 mm or more independently on the vibration frequency of the ultrasonic vibrator 21, a sample with a quantity enough to be injected into the moving liquid can be sampled into the sampling needle 10. On the contrary, when the inner diameter A of the sampling needle 10 is less than 0.1 mm, the amount of the sample that can be sampled into the sampling needle 10 may be too small, and it may be difficult to sample the sample into the sampling needle, depending on the viscosity of the sample, etc.

Additionally, it is preferable that the aforementioned operation in the sample injection apparatus according to the present invention be performed fully-automatically, that is, is an automatic sample injection apparatus.

Now, a specific example of the automatic sample injection apparatus according to the present invention is described with FIG. 1. The automatic sample injection apparatus has a sampling needle 10, a syringe 11, a pump for cleaning liquid 12, a valve 13, a sampling vessel 14, an injection valve 15, a sample loop 16, a cleaning part 17, a cleaning liquid reservoir 18, a cleaning liquid port 24, and needle transfer means that are not shown. In the automatic sample injection apparatus in FIG. 1, the sampling needle 10 is connected to the syringe 11 and a sample supplied into the sampling vessel 14 can be aspirated and ejected by pushing and pulling of the syringe 11. Also, the cleaning liquid stored in the cleaning liquid reservoir 18 is continuously sent to the cleaning part 17 or the sampling needle 10 by the pump for cleaning liquid 12. Herein, the valve 13 is provided between the sampling needle 10 and the syringe 11, and the cleaning liquid sent from the cleaning liquid reservoir 18 can be supplied into the cleaning part 17 or the sampling needle 10 by switching the valve 13. The cleaning liquid is continuously supplied into the cleaning part 17 and the cleaning liquid more than a certain quantity is ejected as waste liquid from the cleaning part 17. An ultrasonic vibrator is attached to the cleaning part 17, which is also fixed on the bottom face of the automatic sample injection apparatus through the intermediary of a vibration buffer spring as a vibration buffer member. The sampling needle 10 is inserted into the injection valve 15, which has an injection port 19 for injecting the sample or the cleaning liquid from the sampling needle 10 and to which the sample loop 16 is connected. Also, liquid is supplied to the injection valve 15 from the outside of the automatic sample injection apparatus and the liquid is sent to the outside of the automatic sample injection apparatus. More specifically, when the automatic sample injection apparatus is used in a liquid chromatography apparatus, solvent as a mobile phase is supplied by a pump provided at the outside of the automatic sample injection apparatus and the solvent is sent to a separation column. Further, one or more cleaning liquid ports 24 (three cleaning liquid ports 24 in FIG. 1) may be provided in the automatic sample injection apparatus (in this case, post-injection washing as one of the aforementioned self-cleaning functions can be performed).

Figure 2:
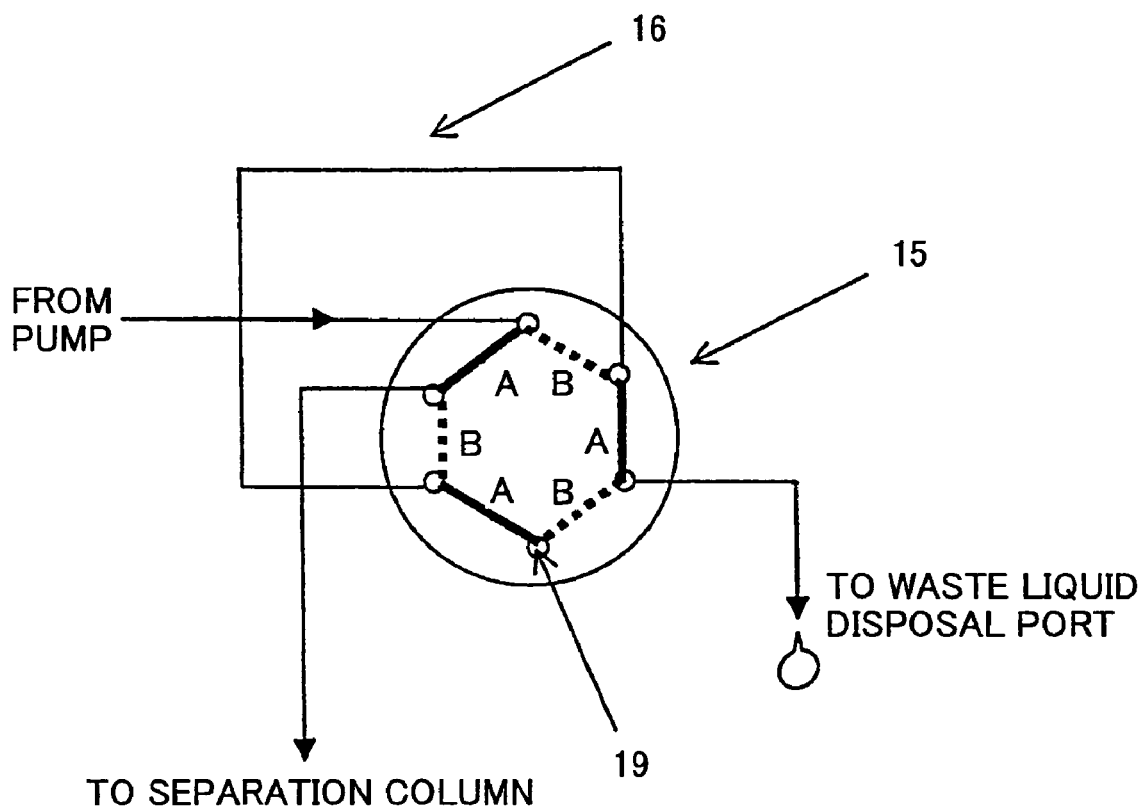
FIG. 2 is a diagram illustrating the operation of an injection valve.

Herein, the operation of the injection valve in the case of being used in a liquid chromatography apparatus is described in detail using FIG. 2. The injection valve 15 has six ports and these six ports are connected as the combination of either solid lines A or broken lines B. The injection valve 15 can switch the connection shown by solid lines A and the connection shown by broken lines B. Additionally, the cleaning liquid is the same as the solvent as a mobile phase in the following description.

When the six ports in the injection valve 15 are connected as shown by solid lines A, the solvent as a mobile phase supplied by an external pump is sent to the separation column. On the other hand, when a sample is supplied to the injection port 19 by the sampling needle, the supplied sample is held in the sample loop 16. Additionally, the length of the sample loop 16 is designed to be able to hold the maximum quantity of sample that can be supplied from the sampling needle. Instead of supplying the sample from the sampling needle, when the cleaning liquid is supplied, the cleaning liquid is continuously supplied from the sample needle and ejected to a waste liquid disposal port through the sample loop 16. That is, the inside of the sample loop 16 can be cleaned with the cleaning liquid.

As the connection of the six ports in the injection valve 15 is switched as shown in broken lines B, the solvent as a mobile phase supplied from the outside of the automatic sample injection apparatus passes through the sample loop 16 and is sent to the separation column. At this time, if the sample is held in the sample loop 16, it is sent to the separation column with the solvent as a mobile phase passing through the sample loop 16. Thus, components of the sample can be separated in the separation column so as to detect the components on a detector. On the other hand, the cleaning liquid is supplied into the injection port 19 through the sampling needle. Accordingly, a flow channel from the injection port 19 to the waste liquid disposal port can be cleaned.

All the flow channels connecting the six ports can be cleaned with the cleaning liquid (the solvent as a mobile phase) by switching the connection of the aforementioned six ports between A and B, since the cleaning liquid is the same as the solvent as a mobile phase. Simultaneously, the injected sample can be sent to the separation column so as to separate and analyze the components of the sample.

Next, a sample injection method according to the present invention is described. First, while a sample is aspirated into a sampling needle and the sample is held in the sampling needle, the sampling needle is dipped in cleaning liquid. Then, an ultrasonic wave is generated in the cleaning liquid so that the sampling needle dipped in the cleaning liquid is cleaned. Afterward, the sample is ejected from the sampling needle and injected into moving liquid.

Figure 3:
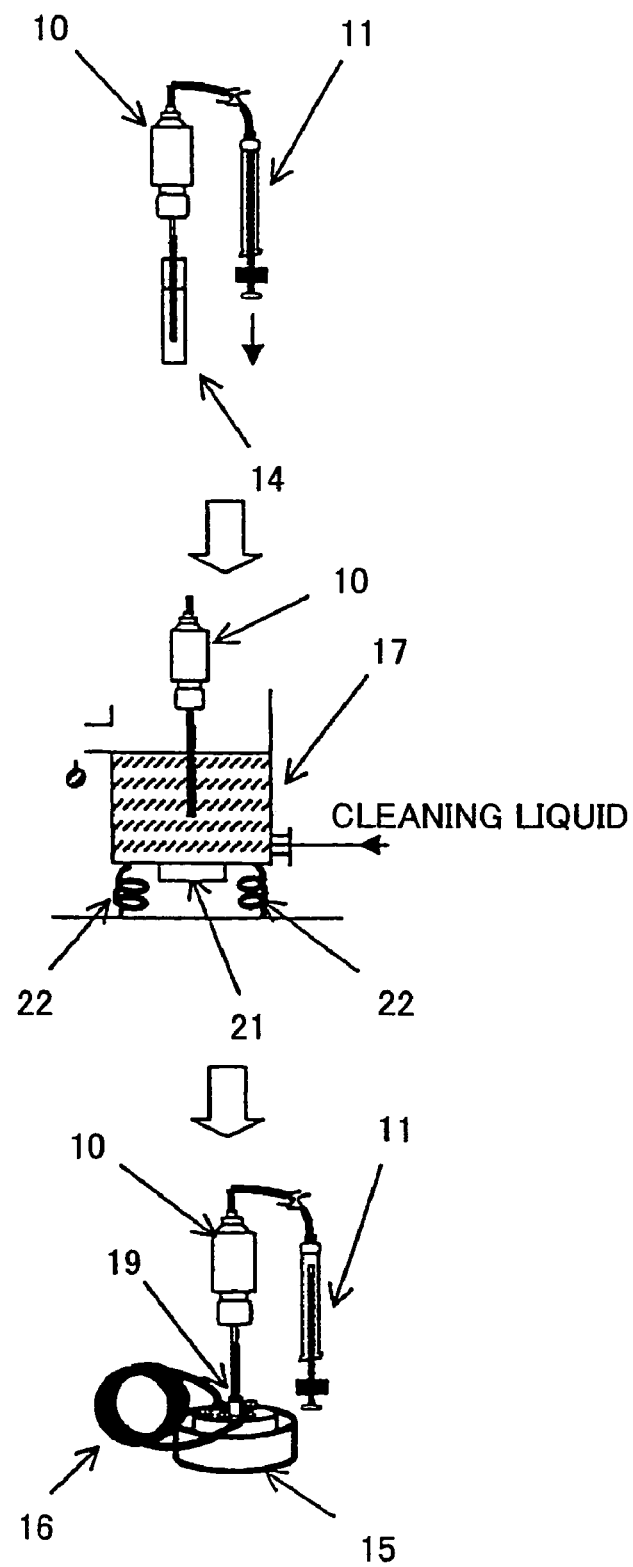
FIG. 3 is a diagram illustrating a sample injection method according to the present invention.

Now, a sample injection method according to the present invention using a sample injection apparatus according to the present invention is described with FIG. 3. First, a previously cleaned sample injecting needle 10 is transferred to a sampling vessel 14 by needle transfer means and dipped into a sample supplied into the sampling vessel 14. Next, a syringe 11 connected to the sampling needle 10 is pulled so as to aspirate the sample into the sampling needle 10. After aspirating the sample, the sampling needle 10 is transferred to a cleaning part 17 using the needle transfer means and dipped into the cleaning liquid supplied into the cleaning part. The cleaning liquid flows through the cleaning part 17 and pure cleaning liquid is continuously supplied into the cleaning part 17. Herein, an ultrasonic vibrator 21 attached to the cleaning part 17 is vibrated so as to generate an ultrasonic wave in the cleaning part. Thus, an outer wall of the sampling needle 10 dipped into the cleaning liquid can be cleaned due to the ultrasonic wave generating in the cleaning liquid. Additionally, even if the outer wall of the sampling needle 10 is cleaned by means of the aforementioned ultrasonic cleaning while the aspirated sample is held in the sampling needle 10, there is no loss of the aspirated sample to the cleaning liquid at all since the sampling needle 10 itself is not vibrated. Also, a vibration buffer spring 22 being a vibration buffer member is attached to the cleaning part, so as to reduce the propagation of vibration of the ultrasonic vibrator 21 to a member other than the cleaning part 17 in the sample injection apparatus. After the sampling needle 10 is subjected to the ultrasonic cleaning, the sampling needle 10 is transferred to an injection valve 15 being a sample injection part using the needle transfer means and the sampling needle 10 is inserted into an injection port 19 of the injection valve 15. Finally, the syringe 11 connected to the sampling needle 10 is pushed, so that the sample sampled into the sampling needle 10 is injected into the moving liquid through the injection valve 15 and the sample loop 16 provided to the injection valve 15.

According to a sample injection apparatus and/or sample injection method according to the present invention, carryover can be sufficiently reduced. Also, since it is not necessary to use the conventional four self-cleaning functions (the needle pre-washing, the needle post-washing, the post-injection washing, and the loop rinse), the sample injection apparatus can be made simple and the condition of cleaning can be easily set. Also, cleaning time period can be shortened relative to cleaning in which the conventional four self-cleaning functions are used. However, if necessary, one or more of the conventional four self-cleaning functions may be combined with the ultrasonic cleaning for the sampling needle according to the present invention. Further, since the sampling needle itself is not vibrated, the durability of the sampling needle is not lowered. Also, there is no loss of the sample aspirated into the sampling needle to the cleaning liquid at all which loss is caused by the vibration of the ultrasonic vibrator and an error in the amount of the injected sample is also small. Moreover, if a vibration buffer member is provided for the cleaning part, the influence of the vibration on a member other than the cleaning part in the sample injection apparatus can be further reduced.

Figure 4:
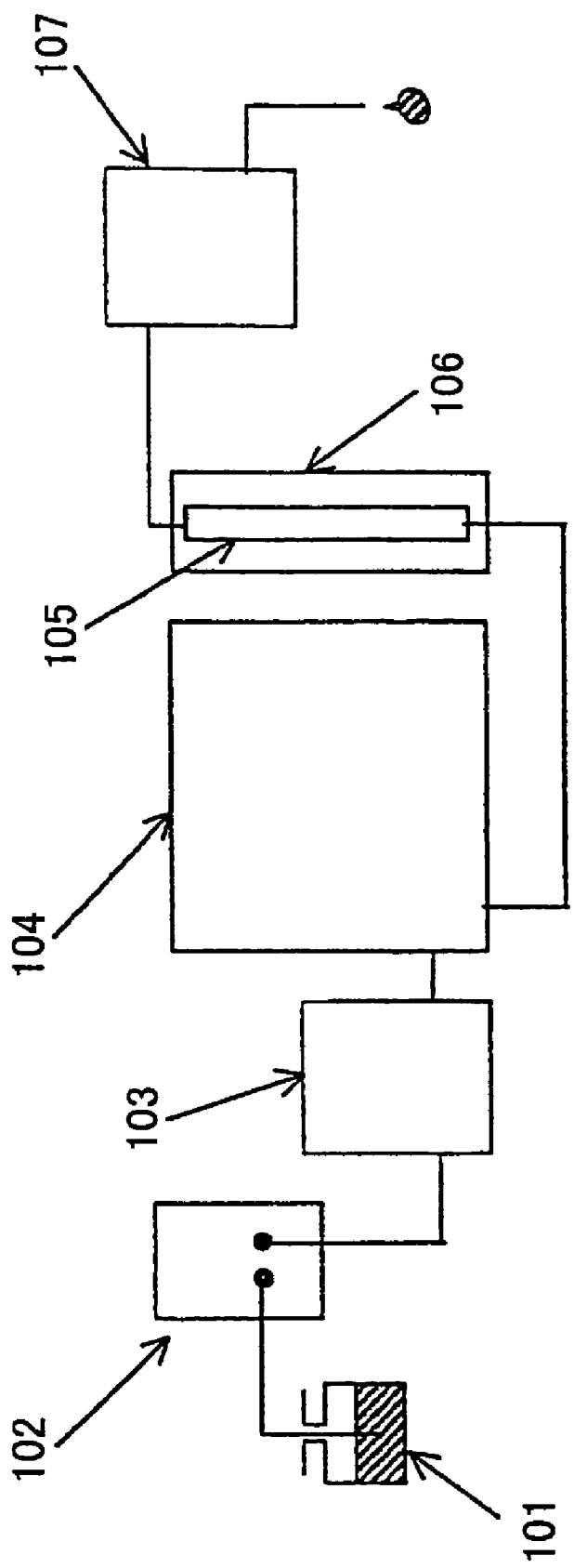
FIG. 4 is a diagram illustrating a liquid chromatography apparatus.

Next, a liquid chromatography apparatus according to the present invention is described with FIG. 4. As shown in FIG. 4, the liquid chromatography apparatus according to the present invention has at least a mobile phase reservoir 101, a sample injection apparatus 104, a separation column 105 and a detector 107, and a sample injection apparatus according to the present invention is used for the sample injection apparatus 104. Commonly used liquid as a mobile phase used for liquid chromatography is stored in the mobile phase reservoir 101. The sample injection apparatus according to the present invention has a function of cleaning a sampling needle by means of an ultrasonic wave and injects a sample into the liquid as a mobile phase, as described above. The separation column 105, in which commonly used column packing material as a stationary phase is filled, separates components of the sample sent from the sample injection apparatus 104 with the liquid as a mobile phase. The detector 107 detects the components of the sample which components are separated by the separation column 105. Herein, mobile phase sending means such as a pump 103 provided between the mobile phase reservoir 101 and the sample injection apparatus 104 is used in order to send the liquid as a mobile phase stored in the mobile phase reservoir 101 to the detector 107. Also, it is preferable that air contained in the liquid as a mobile phase be degassed by a commonly used mobile phase degassing device 102 provided between the mobile phase reservoir 101 and the mobile phase sending means such as the pump 103, before the liquid as a mobile phase is sent to the sample injection apparatus 104 by the mobile phase sending means such as the pump 103. Further, it is desirable that a commonly used column thermostatic bath 106 for keeping the temperature of the separation column 105 constant be provided for the separation column 105 in order to keep the separative power of the separation column 105 such as the number of theoretical plates thereof to be constant.

As a sample injection apparatus in a liquid chromatography apparatus according to the present invention, an automatic sample injection apparatus in accordance with a direct injection approach can be also used. Herein, the structure and operation of an automatic sample injection apparatus in accordance with a direct injection approach are described with FIG. 12.

The automatic sample injection apparatus in accordance with a direct injection approach has a sampling needle 10, a syringe 11, a pump for cleaning liquid 12, a valve 13, a sampling vessel 14, an injection valve 15, a tube 25, cleaning parts 17 and 17', and needle transfer means that are not shown. In the automatic sample injection apparatus in accordance with a direct injection approach shown in FIG. 12, the sampling needle 10 composes a part of the tube 25 for connecting two ports of the injection valve 15. When solvent as a mobile phase flows in the tube 25, the sampling needle 10 is coupled to the tube 25 so as to form a flow channel in which the solvent as a mobile phase flows. On the other hand, when a sample added into the sampling vessel 14 is sampled using the sampling needle 10 and when the sampling needle is cleaned with cleaning liquid supplied into the cleaning part 17 and/or 17', the sampling needle 10 separates from the tube 25 and is transferred to the sampling vessel 14 and the cleaning part 17 and/or 17', respectively, by using the needle transfer means. Also, the syringe 11 is connected to one port of the injection valve 15 and can be connected with the sampling needle 10 by switching the connections between the ports of the injection valve 15. When the syringe 11 is connected to the sampling needle 10, the sampling needle 10 can aspirate and eject the sample supplied into the sampling vessel 14 by push and pull of the syringe 11. Also, the pump for cleaning liquid 12 continuously sends the cleaning liquid stored in a cleaning liquid reservoir to the cleaning part 17 or 17'. Herein, the valve 13 is provided between the injection valve 15 and the syringe 11 and the cleaning liquid sent from the cleaning liquid reservoir can be supplied into the cleaning part 17 or 17' by switching the valve 13. That is, as the injection valve 15 is connected to the pump for cleaning liquid 12 by switching the valve 13, the cleaning liquid is supplied into the cleaning part 17 through a port of the injection valve 15 which port is connected to the cleaning part 17. Also, as the cleaning part 17' is connected to the pump for cleaning liquid 12 by switching the valve 13, the cleaning liquid is supplied into the cleaning part 17'. The cleaning liquid is continuously supplied into the cleaning part 17 or 17' and the cleaning liquid more than a certain quantity is ejected as waste liquid from the cleaning part 17 or 17' through a waste liquid disposal port 23. Also, an ultrasonic vibrator 21 is attached in the neighborhood of the cleaning part 17. An ultrasonic wave can be generated in the cleaning liquid supplied into the cleaning part 17 by vibrating the ultrasonic vibrator 21. Also, solvent as a mobile phase is supplied to the injection valve 15 by a pump 103 provided at the outside of the automatic sample. injection apparatus and the solvent is sent to a separation column 105.

Figure 12:
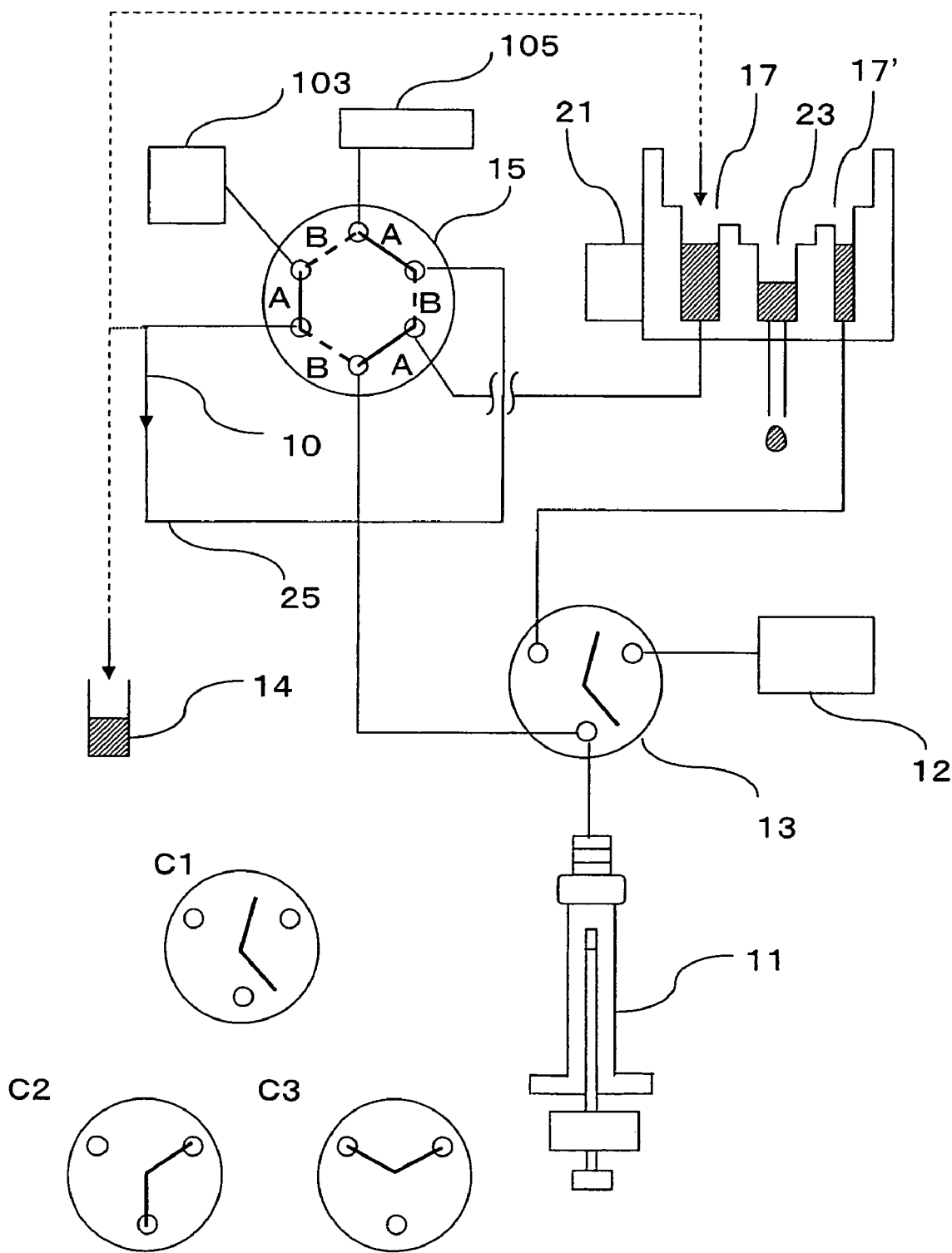
FIG. 12 is a diagram illustrating the structure and operation of an automatic sample injection apparatus in accordance with a direct injection approach.

Next, the operation of the automatic sample injection apparatus in accordance with a direct injection approach is described in detail using FIG. 12.

In the automatic sample injection apparatus in accordance with a direct injection approach, the injection valve 15 also has six ports and these six ports are connected in the combination of either solid lines A or broken lines B. The injection valve 15 can switch the connection shown by solid lines A and the connection shown by broken lines B. Additionally, the cleaning liquid is the same as the solvent as a mobile phase in the following description.

First, the six ports of the injection valve 15 are connected as shown by solid lines A. In this case, the sampling needle 10 is coupled with the tube 25. Then, the solvent as a mobile phase supplied from the external pump 103 is sent to the separation column 105 through a flow channel formed by coupling the sampling needle 10 with the tube 25. Herein, three ports of the valve 13 are not connected together as C1 shown in FIG. 12.

Next, the connections of the six ports of the injection valve 15 are switched as shown by broken lines B. At this time, the solvent as a mobile phase supplied from the external pump 103 is sent to the separation column 105 without passing through the sampling needle 10 or the tube 25. Therefore, the sampling needle 10 is separated from the tube 25 so that sampling of a sample by the sampling needle 10 and the cleaning of the sampling needle 10 are allowed.

First, when a sample supplied into the sampling vessel 14 is sampled using the sampling needle 10, the sampling needle 10 transfers to a position at which the sampling vessel 14 is placed, by using needle transfer means, the tip portion of the sampling needle 10 is dipped in the sample. Herein, since the sampling needle 10 and the syringe 11 are connected through the injection valve 15, an appropriate quantity of the sample can be sampled in the sampling needle 10.

Next, when the sampling needle is cleaned, the sampling needle 10 having sampled the sample is subsequently transferred to the cleaning part 17 and/or 17' using the needle transfer means without pushing or pulling the syringe 11. Then, the tip portion of the sampling needle 10 is dipped into the cleaning part 17 and/or 17'. When the sampling needle 10 transfers to the cleaning part 17 and the tip portion of the sampling needle 10 is dipped into the cleaning part 17, the ultrasonic vibrator 21 attached in the neighborhood of the cleaning part 17 vibrates so as to generate an ultrasonic wave in the cleaning liquid in the cleaning part 17. Thus, an outer surface of the tip portion of the sampling needle 10 can be effectively cleaned by the ultrasonic wave generating in the cleaning liquid in the cleaning part 17. Additionally, there is no loss of the sample sampled and held in the sampling needle 10 to the cleaning liquid at all, since the sampling needle 10 itself does not vibrate even if the ultrasonic wave generates in the cleaning liquid. Then, waste liquid produced by the ultrasonic cleaning for the sampling needle 10 is disposed to the exterior through the waste liquid disposal port 23. On the other hand, when the sampling needle 10 transfers to the cleaning part 17' and is dipped in the cleaning liquid in the cleaning part 17' so that the needle pre-washing for the sampling needle 10 is performed, the valve 13 is in the state of C3 shown in FIG. 12 so that the pump for cleaning liquid 12 is connected to the cleaning part 17' and the cleaning liquid is continuously supplied into the cleaning part 17'. Accordingly, an outer surface of the tip portion of the sampling needle 10 can be cleaned with the cleaning liquid that is continuously supplied into the cleaning part 17'. Then, waste liquid produced by cleaning the sampling needle 10 is disposed to the exterior through the waste liquid disposal port 23.

Next, the sampling needle 10 is transferred to the tube 25 and the sampling needle 10 is coupled to the tube 25 using needle transfer means without pushing or pulling the syringe. Thus, a flow channel for the solvent as a mobile phase supplied from the external pump 103 is formed. Herein, the sample sampled in the sampling needle is injected into the tube 25 by pushing the syringe. After the sampled sample is injected into the tube 25, the connections of the six ports of the injection valve 15 are switched as shown by broken lines A. Accordingly, the solvent as a mobile phase supplied from the external pump 103 flows through the tube 25 and is supplied into the separation column 105 with the sample injected to the tube 25. Then, components of the sample supplied into the separation column 105 with the solvent as a mobile phase are separated in the separation column 105 and the components can be detected on a detector. At the same time, the valve 13 is in the state of C2 or C3 shown in FIG. 12 so that the pump for cleaning liquid 12 is connected to the cleaning part 17 or 17' and the cleaning liquid in the cleaning part 17 or 17' can be exchanged. That is, as the valve 13 is in the state of C2 shown in FIG. 12, the pump for cleaning liquid 12 is connected to the cleaning part 17 so that a certain quantity of the cleaning liquid is supplied into the cleaning part 17. As the result, the cleaning liquid in the cleaning part 17 which liquid remains after the sampling needle 10 is subjected to the ultrasonic cleaning is disposed to the exterior through the waste liquid disposal port 23 and fresh cleaning liquid supplied by the pump for cleaning liquid is supplied into the cleaning part 17. Similarly, as the valve 13 is in the state of C3 shown in FIG. 12, the pump for cleaning liquid 12 is connected to the cleaning part 17' so that a certain quantity of the cleaning liquid is supplied into the cleaning part 17'. As the result, the cleaning liquid in the cleaning part 17' which liquid remains after the needle pre-washing is applied to the sampling needle 10 is disposed to the exterior through the waste liquid disposal port 23 and fresh cleaning liquid supplied by the pump for cleaning liquid is supplied into the cleaning part 17'.

EXAMPLE 1

Figure 5:
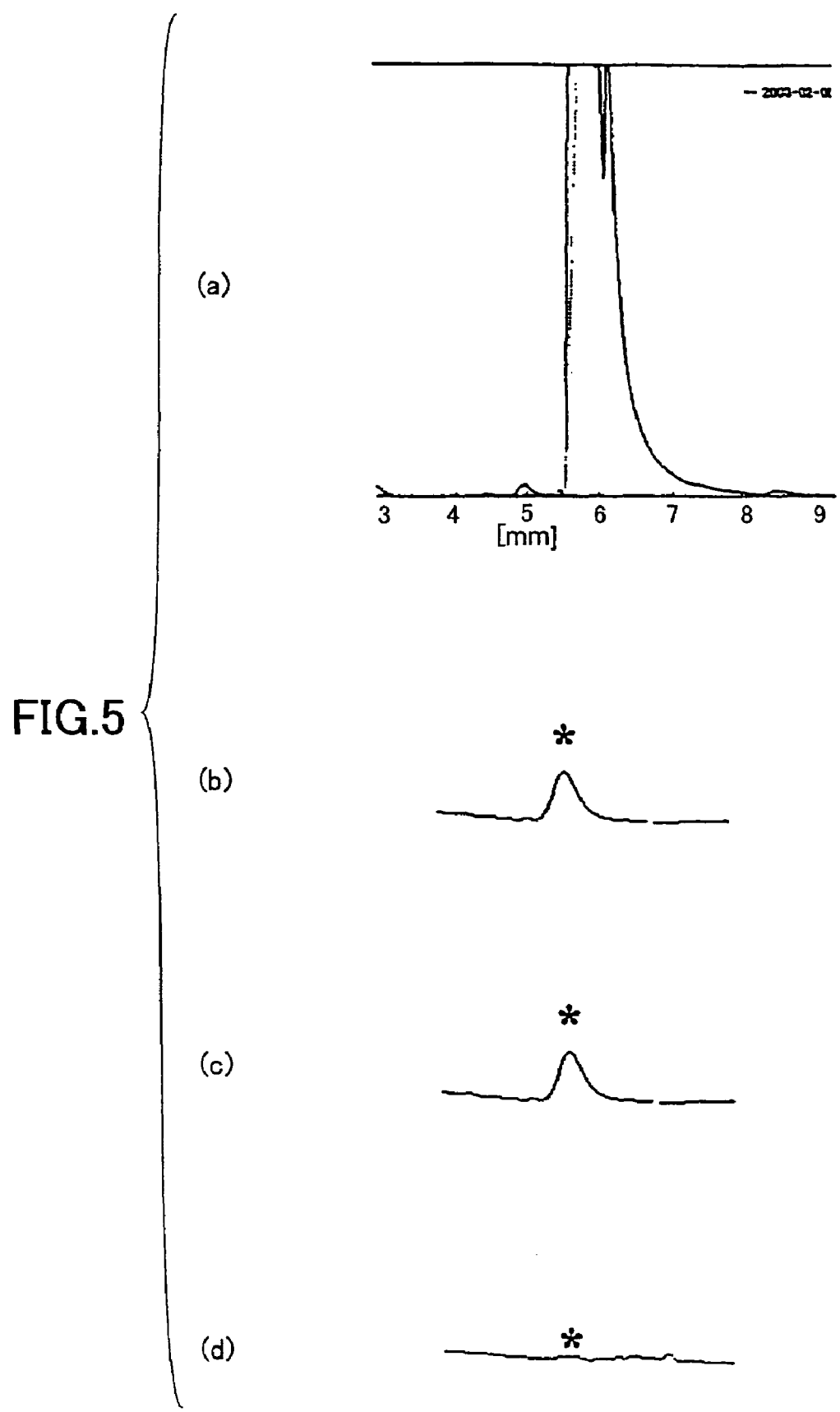
FIG. 5 is a diagram showing evaluation results in regard to carry-over which was performed for a liquid chromatography apparatus, wherein (a) is a diagram showing a peak for a sample, (b) is a diagram showing a detection result in the case of performing the needle pre-washing and the needle post-washing, (c) is a diagram showing a detection result in the case of performing all of the four self-cleaning functions, and (d) is a diagram showing a detection result in the case of only ultrasonic cleaning in accordance with the present invention.
Figure 6:
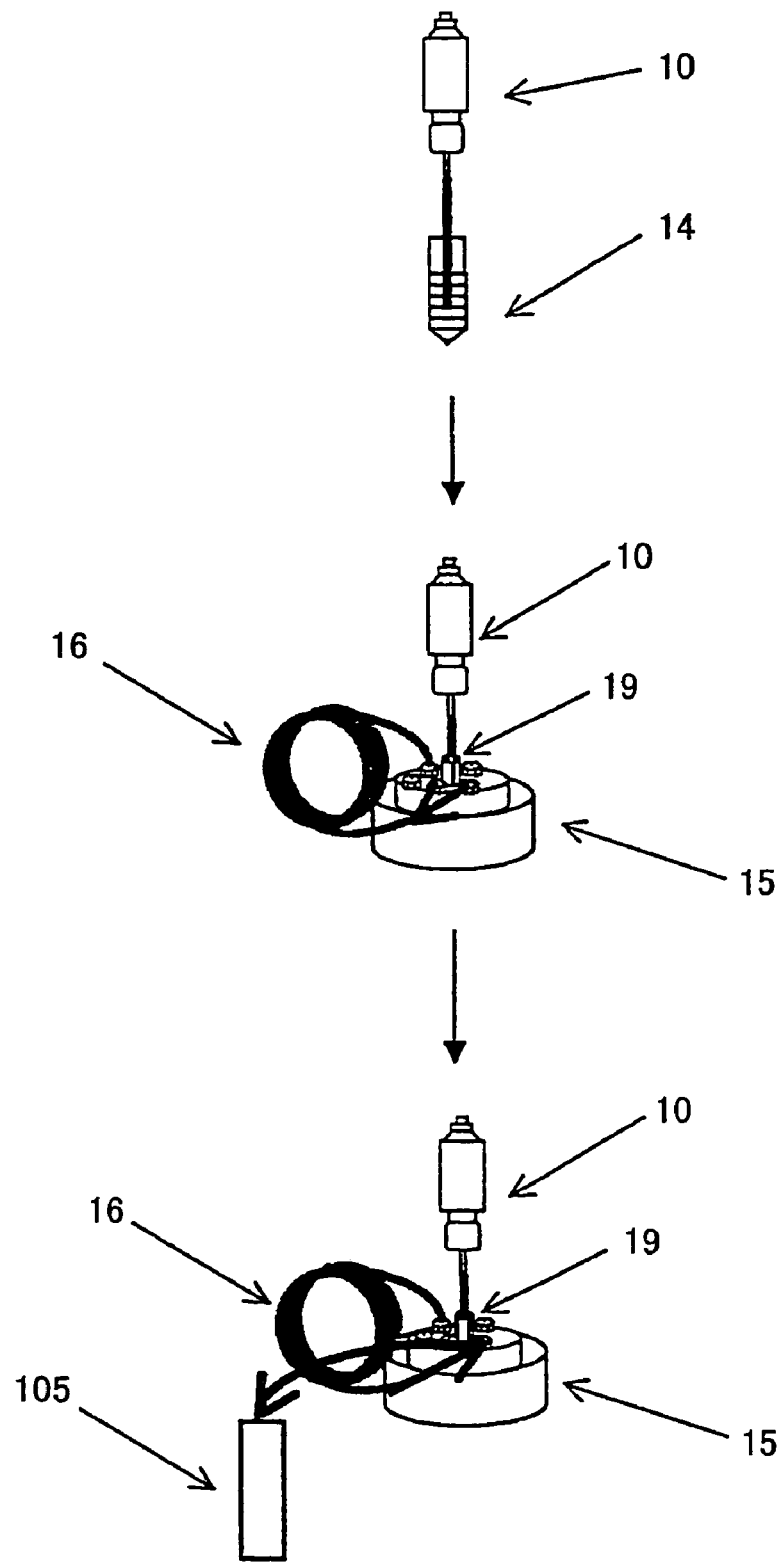
FIG. 6 is a diagram illustrating the main operation of the automatic sample injection apparatus.
Figure 7:
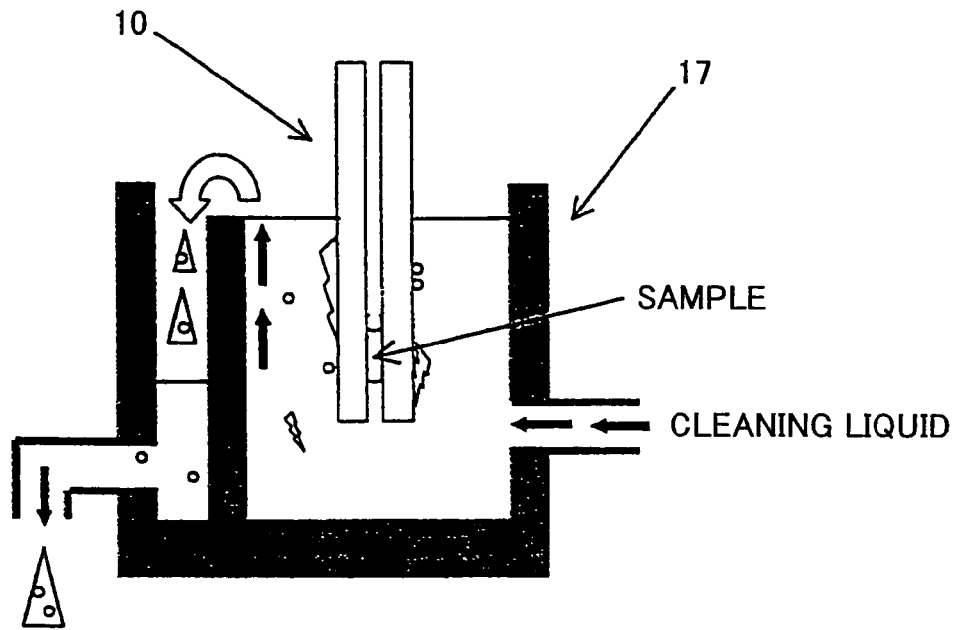
FIG. 7 is a diagram illustrating the needle pre-washing.
Figure 8:
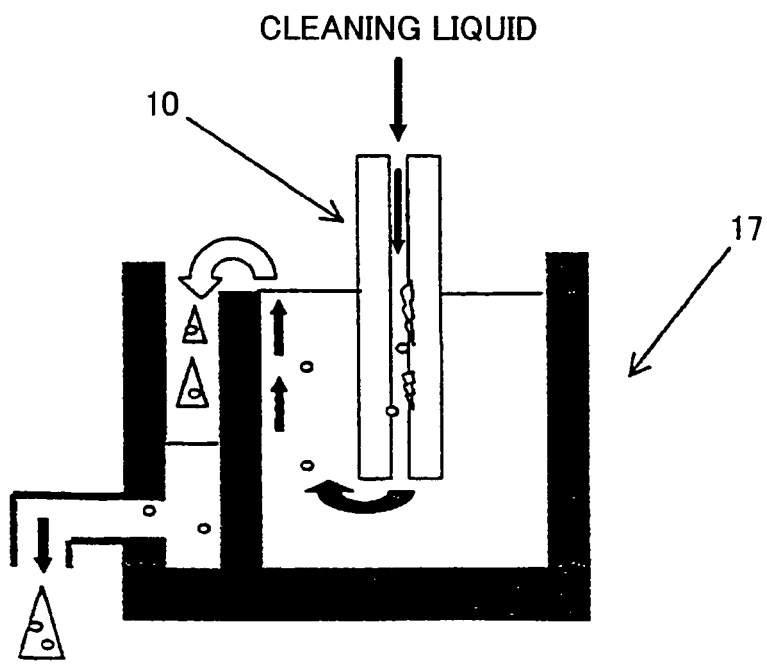
FIG. 8 is a diagram illustrating the needle post-washing.
Figure 9:
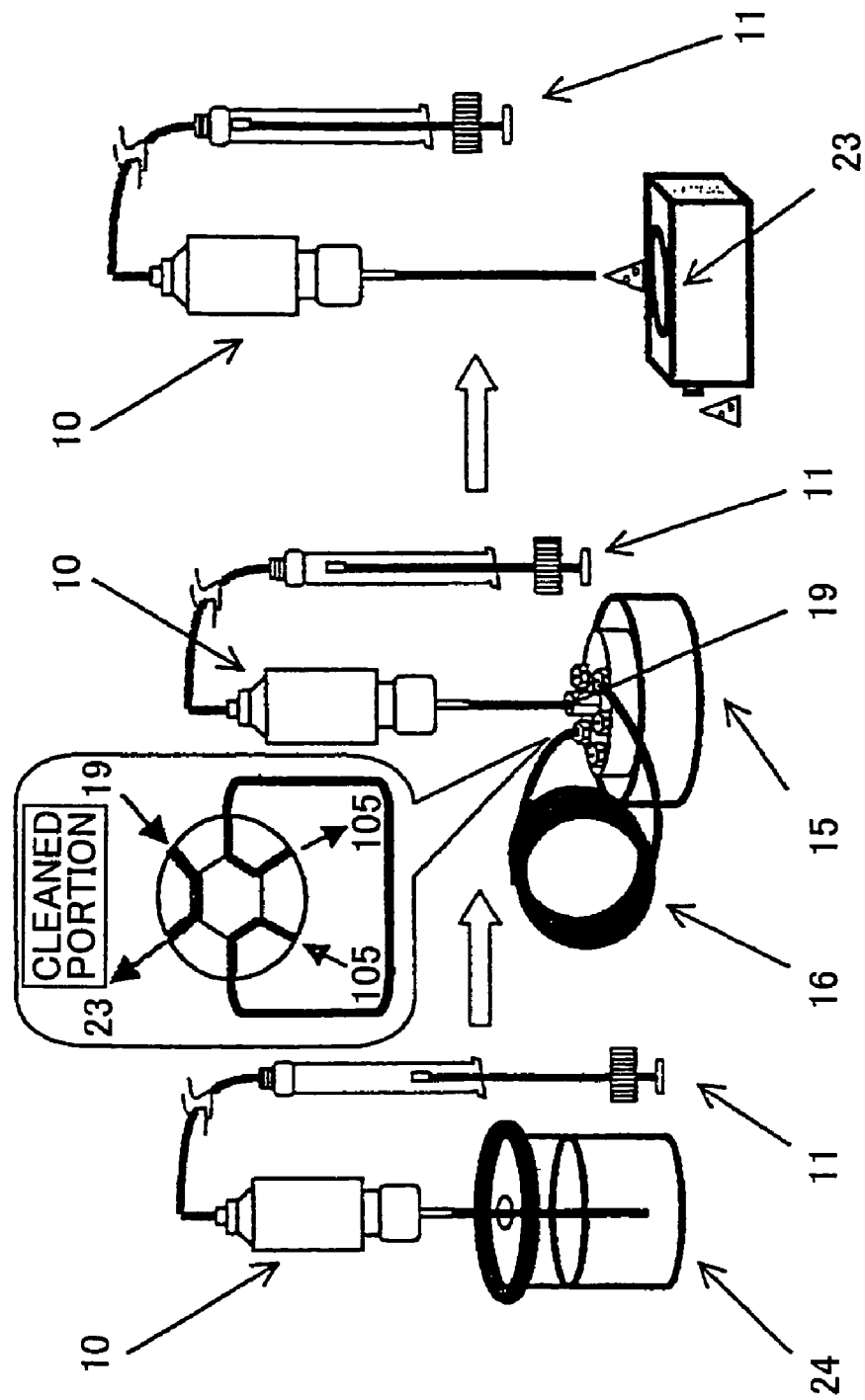
FIG. 9 is a diagram illustrating the post-injection washing.
Figure 11:
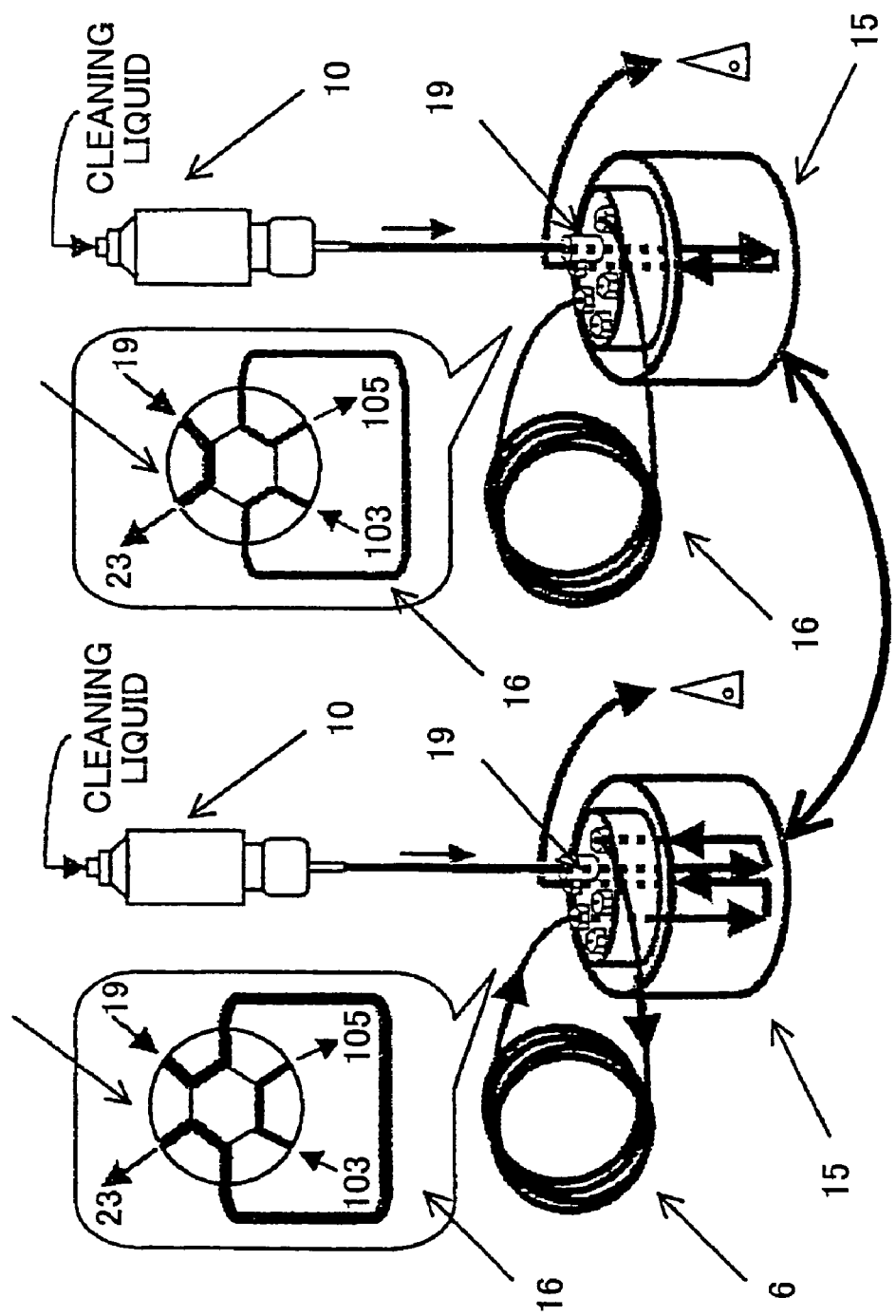
FIG. 11 is a diagram showing cleaning for a sample loop and an injection valve in the loop rinse.

The evaluation result of carry-over performed for a liquid chromatography according to the present invention is described with FIG. 5.

The evaluation of carry-over was performed using a liquid chromatography apparatus as shown in FIG. 4 provided with an automatic sample injection apparatus as shown in FIGS. 1 through 3. For a solvent as a mobile phase for the liquid chromatography, a mixed solvent of 100 mM of $NaClO_4$ and 10 mM of $MH_4H_2PO_4$ (pH 2.6)/$CH_3CN$ (volume ratio 55:45) was used. Also, the velocity of flow of the solvent as a mobile phase was 0.2 ml/min. Additionally, a mixed solvent with the same composition as that of the solvent as a mobile phase was used for cleaning liquid. For the separation column 105, a column with an inner diameter of 2 mm×a length of 150 mm was used and the temperature of the separation column 105 was kept at 40° C. using the column thermostatic bath 106. For a column packing material as a stationary phase for the liquid chromatography, octadecylated silica gel with a particle diameter of 5 microns was used. As a sample for evaluating the carry-over, basic and hydrophobic chlorhexidine represented by

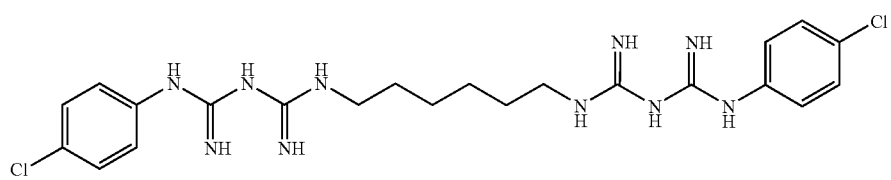

was used, whereby the carry-over was easy to make occur. For the detector 107 for detecting the chlorhexidine, an absorptiometric detector using ultraviolet rays with a wavelength of 260 nm was used.

First, it was confirmed that the amount of the sample injected into the mobile phase was not changed by ultrasonic cleaning according to the present invention. 2 μl of 12 ppm chlorhexidine as a sample was sampled in the sampling needle 10, then the sampling needle 10 was dipped into a cleaning part, and simultaneously an outer wall of the sampling needle 10 was subjected to ultrasonic cleaning, and subsequently, the sampled sample was injected into the mobile phase. Herein, the amount of the injected sample that was detected when the sampling needle 10 was subjected to the ultrasonic cleaning did not change compared to that when the sampling needle was not subjected to the ultrasonic cleaning. Therefore, it was confirmed that the amount of the sample injected into the mobile phase was not reduced by the ultrasonic cleaning according to the present invention.

Next, the evaluation of carry-over in a sample injection apparatus according to the present invention was performed. The evaluation results of the carry-over are shown in FIG. 5. First, 2 μl of chlorhexidine with a high concentration of 1200 ppm as a sample was sampled in the sampling needle and was injected into the mobile phase and a peak for chlorhexidine was detected. Next, 2 μl of the same solvent as the mobile phase which contained no chlorhexidine (referred to as a blank sample, below) was injected and the presence or absence of the remaining chlorhexidine (carry-over) was observed. At this time, cleanings shown in the following (1), (2) and (3) were performed.

(1) After 2 μl of chlorhexidine with a high concentration of 1200 ppm was sampled in the sampling needle, the needle pre-washing was performed and, subsequently, the sampled sample was injected into the mobile phase. Afterward, the needle post-washing was applied to the sampling needle and, subsequently, the blank sample was sampled and injected into the mobile phase.

(2) After 2 μl of chlorhexidine with a high concentration of 1200 ppm was sampled in the sampling needle, the needle pre-washing was performed, and subsequently the sampled sample was injected into the mobile phase. Afterward, the needle post-washing, the post-injection washing and the loop rinse were applied to the sampling needle, and subsequently the blank sample was sampled and injected to the mobile phase.

(3) After 2 μl of chlorhexidine with a high concentration of 1200 ppm was sampled in the sampling needle, the ultrasonic cleaning according to the present invention was preformed and, subsequently, the sampled sample was injected into the mobile phase. Afterward, the blank sample was sampled and injected into the mobile phase without cleaning the sampling needle.

A peak for chlorhexidine detected when 2 μl of chlorhexidine with a high concentration of 1200 ppm was injected into the mobile phase is shown in FIG. 5(a). Also, the measurement results of carry-over (remaining chlorhexidine) after the injection of the blank sample in (1) the case of performing the needle pre-washing and needle post-washing, (2) the case of performing all the aforementioned four self-cleaning functions, and (3) the case of performing only the ultrasonic cleaning according to the present invention, described above, are shown in FIGS. 5(b), (c) and (d), respectively. Additionally, the horizontal axis is relative detection time and the vertical axis is an absorbance proportional to the concentration of chlorhexidine in FIGS. 5(a) through (d).

Herein, if there was no carry-over, no peak for the remaining chlorhexidine should be measured. As shown in FIG. 5(b), in the case of performing the conventional needle pre-washing and needle post-washing, the remaining chlorhexidine, that is, the carry-over was detected. The detected remaining chlorhexidine was not eliminated even when the needle pre-washing was applied to the sampling needle for a long time period (5 seconds or more). Next, as shown in FIG. 5(c), in the case of performing all the conventional four self-cleaning functions, no remaining chlorhexidine was detected and the carry-over was eliminated, but a cleaning time period of 3.9 minutes was required in order to perform all the four self-cleaning functions. Finally, as shown in FIG. 5(d), in the case of performing only the ultrasonic cleaning according to the present invention, while no remaining chlorhexidine was detected and the carry-over was eliminated, the cleaning time period of the ultrasonic cleaning was 20 seconds.

From the results described above, the carry-over could be reduced to the same degree as the case of performing all the four self-cleaning functions and the cleaning time period could be shortened by performing the ultrasonic cleaning according to the present invention for the sampling needle in the liquid chromatography apparatus according to the present invention. Also, since it is only necessary to subject an outer wall of the sampling needle to the ultrasonic cleaning, cleaning processes can be simplified.

EXAMPLE 2

The results of carry-over evaluation performed for a liquid chromatography apparatus including an automatic sample injection apparatus in accordance with a direct injection approach is described with FIG. 13.

The evaluation for carry-over was performed using a liquid chromatography apparatus as shown in FIG. 4 provided with an automatic sample injection apparatus in accordance with a direct injection approach as shown in FIG. 12, similar to example 1.

That is, for a solvent as a mobile phase of the liquid chromatography, a mixed solvent of 100 mM of $NaClO_4$ and 10 mM of $MH_4H_2PO_4$ (pH 2.6)/$CH_3CN$ (volume ratio 55:45) was used. Also, the velocity of flow of the solvent as a mobile phase was 0.2 ml/min. A mixed solvent with the same composition as that of the solvent as a mobile phase was used for cleaning liquid. For the separation column 105, a column with an inner diameter of 2 mm×a length of 150 mm was used and the temperature of the separation column 105 was kept at 40° C. using the column thermostatic bath 106. For a column packing material as a stationary phase for the liquid chromatography, octadecylated silica gel with a particle diameter of 5 microns was used. As a sample for evaluating the carry-over, chlorhexidine was used. For the detector 107 for detecting the chlorhexidine, an absorptiometric detector using ultraviolet rays with a wavelength of 260 nm was used.

The evaluation results of the carry-over are shown in FIG. 13. First, 2 μl of chlorhexidine with a high concentration of 1200 ppm as a sample was sampled in the sampling needle and was injected into the mobile phase and a peak for chlorhexidine was detected. Next, 2 μl of the same solvent as the mobile phase which contained no chlorhexidine (referred to as a blank sample, below) was injected and the presence or absence of the remaining chlorhexidine (carry-over) was observed.

At this time, cleanings shown in the following (1) and (2) were performed.

(1) After 2 μl of chlorhexidine with a high concentration of 1200 ppm was sampled in the sampling needle, only the ultrasonic cleaning according to the present invention was preformed and, subsequently, the sampled sample was injected into the mobile phase. Afterward, the blank sample was sampled and injected into the mobile phase without cleaning the sampling needle.

(2) After 2 μl of chlorhexidine with a high concentration of 1200 ppm was sampled in the sampling needle, only the needle pre-washing was performed and, subsequently, the sampled sample was injected into the mobile phase. Afterward, the blank sample was sampled and injected into the mobile phase without cleaning the sampling needle.

When 2 μl of chlorhexidine with a high concentration of 1200 ppm was injected to the mobile phase, the detected peak for chlorhexidine is shown in FIG. 13(a). Also, the measurement results of carry-over (remaining chlorhexidine) after the injection of the blank sample in (1) the case of performing only the ultrasonic cleaning according to the present invention, and (2) the case of performing only the needle pre-washing, described above, are shown by P1 and P2 of FIG. 13(b), respectively. Additionally, the horizontal axis is relative detection time period (minute(s)) and the vertical axis is an absorbance proportional to the concentration of chlorhexidine in FIGS. 13(a) and (b).

As shown by P2 of FIG. 13(b), in the case of performing only the conventional needle pre-washing, the remaining chlorhexidine, that is, the carry-over was detected. On the other hand, as shown by P1 of FIG. 13(b), in the case of performing only the ultrasonic cleaning according to the present invention, no remaining chlorhexidine was detected and the carry-over was eliminated.

From the results described above, the carry-over could be sufficiently reduced by performing the ultrasonic cleaning for a sampling needle according to the present invention, also in the liquid chromatography apparatus including an automatic sample injection apparatus in accordance with a direct injection approach.

Figure 15:
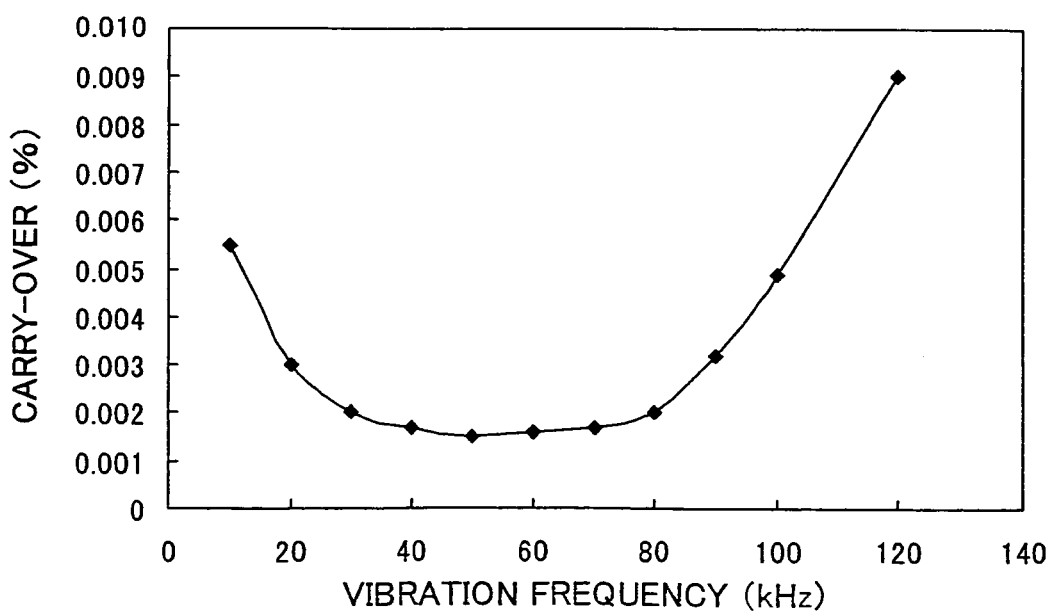
FIG. 15 is a diagram showing the relation between the vibration frequency of an ultrasonic vibrator for ultrasonic cleaning in the present invention and carry-over.

Further, in regard to the ultrasonic cleaning according to the present invention described in (1) of example 2, the evaluation of carry-over was performed while the vibration frequency of an ultrasonic vibrator provided on a cleaning part of the sample injection apparatus was changed. FIG. 15 shows the relation between the vibration frequency of the ultrasonic vibrator for the ultrasonic cleaning according to the present invention shown in (1) of example 2 and the carry-over. Additionally, the horizontal axis represents the vibration frequency (kHz) of the ultrasonic vibrator provided on the cleaning part of the sample injection apparatus and the vertical axis represents the carry-over, that is, the percentage (%) of the amount of chlorhexidine detected after the blank sample was injected into the mobile phase relative to the injection amount 2 μl of chlorhexidine with a high concentration of 1200 ppm injected into the mobile phase in FIG. 15. Therefore, the smaller the value of the carry-over (%) is, the smaller the amount of chlorhexidine detected after the blank sample is injected is and the more effectively the carry-over is reduced. The vibration frequencies of the ultrasonic vibrator were set to 10 kHz, 20 kHz, 30 kHz, 40 kHz, 50 kHz, 60 kHz, 70 kHz, 80 kHz, 90 kHz, 100 kHz, and 120 kHz, respectively. Also, the output of vibration of the ultrasonic vibrator was 50 W. The result of change of the carry-over relative to the vibration frequencies of the ultrasonic vibrator is shown in FIG. 15. As shown in FIG. 15, it was confirmed that, in regard to the ultrasonic cleaning according to the present invention described in (1) of example 2, when the vibration frequency of the ultrasonic vibrator was 20 kHz or more and 80 kHz or less, the carry-over was small, and when the vibration frequency of the ultrasonic vibrator was less than 20 kHz or more than 80 kHz, the carry-over became slightly larger. That is, when the vibration frequency of the ultrasonic vibrator was 20 kHz or more and 80 kHz or less, the carry-over was reduced more efficiently.

Figure 16:
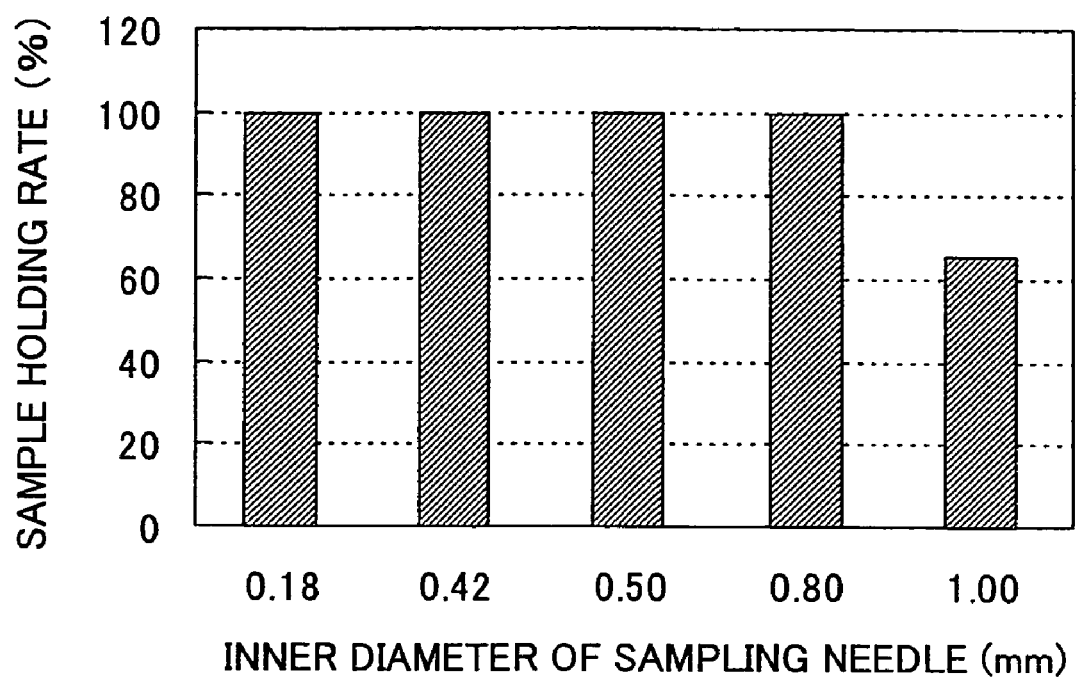
FIG. 16 is a diagram showing the relation between the inner diameter and sample retention of a sampling needle.

Further, in regard to the ultrasonic cleaning according to the present invention described in (1) of example 2, chlorhexidine with a concentration of 60 ppm (standard sample) was used instead of chlorhexidine with a high concentration of 1200 ppm and the evaluation for loss of the standard sample held in the sampling needle which loss was caused by an ultrasonic wave was performed while the inner diameter of the sampling needle was changed. FIG. 16 shows the relation between the inner diameter of the sampling needle and the retention of the sample. Additionally, the horizontal axis represents the inner diameter (mm) of the sampling needle and the vertical axis represents the retention (%) of the standard example held in the sampling needle, that is, the ratio of the volume of the standard sample held in the sampling needle in the case of generating an ultrasonic wave in the cleaning liquid in the cleaning part relative to the volume of the standard sample held in the sampling needle in the case of generating no ultrasonic wave in the cleaning liquid in the cleaning part, in FIG. 16. Therefore, the higher the retention (%) of the standard sample held in the sampling needle is, the smaller the loss of the standard sample held in the sampling needle which loss was caused by the ultrasonic wave is. The inner diameters of the sampling needle were 0.18 mm, 0.42 mm, 0.50 mm, 0.80 mm, and 1.00 mm, respectively. Also, the vibration frequency of the ultrasonic vibrator was 80 kHz. As shown in FIG. 16, when the inner diameter of the sampling needle was 0.80 mm, the retention (%) of the standard sample held in the sampling needle was generally 100%, and there was no loss of the standard sample held in the sampling needle which loss was caused by the ultrasonic wave. On the other hand, when the inner diameter of the sampling needle was larger than 0.80 mm (was 1.00 mm), a part of the standard sample held in the sampling needle was lost by the ultrasonic wave and the retention of the standard sample held in the sampling needle was 65%.

Thus, the embodiment and example of the present invention has been specifically described above, but the present invention is not limited to the embodiment and example and the embodiment and example of the present invention can be modified or altered without deviating from the essence and scope of the present invention.

INDUSTRIAL APPLICABILITY

The present invention can be applied to a sample injection apparatus and sample injection method capable of sufficiently reducing carry-over, having simple cleaning means for a short cleaning time period, a small influence of vibration of the cleaning means, and a small error in the amount of injected sample and preventing the durability of a sampling needle from being lowered, and a liquid chromatography apparatus having the sample injection apparatus.

The invention claimed is:
1. A sample injection apparatus comprising:
   a sampling vessel configured to hold a sample;
   a sampling needle configured to aspirate the sample held by the sampling vessel and to eject the sample;
   a cleaning part configured to receive a cleaning liquid which cleans at least the sampling needle;
   a sample injection part configured to inject the sample ejected from the sampling needle into a moving liquid; and a needle transfer part configured to transfer the sampling needle among the sampling vessel, the cleaning part and the sample injection part, so that the sampling needle is dipped into the cleaning liquid in the cleaning part in a state where the sampling needle holds the sample, and the needle thereafter ejects the sample which is injected into the moving liquid by the sample injection part, wherein the cleaning part comprises an ultrasonic vibrator configured to generate ultrasonic waves in the cleaning liquid.

2. The sample injection apparatus as claimed in claim 1, wherein the cleaning part comprises a vibration buffer member configured to reduce propagation of vibration caused by the ultrasonic vibrator to a member other than the cleaning part in the sample injection apparatus.

3. The sample injection apparatus as claimed in claim 1, wherein a vibration frequency of the ultrasonic vibrator is 20 kHz or more and 80 kHz or less.

4. The sample injection apparatus as claimed in claim 3, wherein an inner diameter of the sampling needle is 0.1 mm or more and 0.8 mm or less.

5. A liquid chromatography apparatus comprising a mobile phase reservoir configured to store a liquid as a mobile phase, a sample injection apparatus configured to inject a sample into the liquid as a mobile phase, a separation column configured to separate a component of the sample supplied from the sample injection apparatus and the liquid as the mobile phase, and a detector configured to detect a component of the sample separated by the separation column, wherein the sample injection apparatus comprises:

a sampling vessel configured to hold the sample, a sampling needle configured to aspirate the sample held by the sampling vessel and to eject the sample, a cleaning part configured to receive a cleaning liquid which cleans at least the sampling needle, a sample injection part configured to inject the sample ejected from the sampling needle into the liquid as the mobile phase, and a needle transfer part configured to transfer the sampling needle among the sampling vessel, the cleaning part and the sample injection part, so that the sampling needle is dipped into the cleaning liquid in the cleaning part in a state where the sampling needle holds the samples and the needle thereafter ejects the sample which is injected into the moving liquid by the sample injection part, wherein the cleaning part comprises an ultrasonic vibrator configured to generate ultrasonic waves in the cleaning liquid.

6. The liquid chromatography apparatus as claimed in claim 5, wherein the cleaning part comprises a vibration buffer member configured to reduce propagation of vibration caused by the ultrasonic vibrator to a member other than the cleaning part in the sample injection apparatus.

7. The liquid chromatography apparatus as claimed in claim 5, wherein a vibration frequency of the ultrasonic vibrator is 20 kHz or more and 80 kHz or less.

8. The liquid chromatography apparatus as claimed in claim 7, wherein an inner diameter of the sampling needle is 0.1 mm or more and 0.8 mm or less.

\* \* \* \* \*